(12) United States Patent
Stone et al.

(10) Patent No.: US 10,722,169 B2
(45) Date of Patent: Jul. 28, 2020

(54) PHYSIOLOGICAL CONDITION DETERMINATION BASED ON PRESSURE WAVE PRODUCED BY AN IMPLANTABLE MEDICAL DEVICE HOUSING

(75) Inventors: Richard T. Stone, Minneapolis, MN (US); Xuan Wei, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 1102 days.

(21) Appl. No.: 13/982,159

(22) PCT Filed: Jan. 24, 2012

(86) PCT No.: PCT/US2012/022388
§ 371 (c)(1),
(2), (4) Date: Jul. 26, 2013

(87) PCT Pub. No.: WO2012/103108
PCT Pub. Date: Aug. 2, 2012

(65) Prior Publication Data
US 2013/0310706 A1   Nov. 21, 2013

Related U.S. Application Data

(60) Provisional application No. 61/437,299, filed on Jan. 28, 2011.

(51) Int. Cl.
*A61B 5/00* (2006.01)
*A61B 5/20* (2006.01)
(Continued)

(52) U.S. Cl.
CPC .......... *A61B 5/4836* (2013.01); *A61B 5/0004* (2013.01); *A61B 5/202* (2013.01);
(Continued)

(58) Field of Classification Search
None
See application file for complete search history.

(56) References Cited

U.S. PATENT DOCUMENTS

| 4,852,578 A | 8/1989 | Companion et al. |
| 4,911,172 A | 3/1990 | Bui et al. |

(Continued)

FOREIGN PATENT DOCUMENTS

| DE | 3932718 A1 | 4/1991 |
| EP | 1808130 A1 | 7/2007 |

(Continued)

OTHER PUBLICATIONS

Freudenrich, Craig, C, "How Ultrasound Works", http://www.physics.utoronto.ca/~jharlow/teaching/phy138_0708/lec04/ultrasoundx.htm, Feb. 1, 2001, 9 pages.*

(Continued)

*Primary Examiner* — Matthew Kremer
(74) *Attorney, Agent, or Firm* — Shumaker & Sieffert, P.A.

(57) ABSTRACT

A physiological state of a patient is detected by at least producing and detecting pressure waves with a free wall of an implantable medical device (IMD) housing. An actuator element may contact the free wall, e.g., a portion of the IMD housing, and cause movement of the free wall that produces a pressure wave within the fluid and tissue of the patient. A detector element contacting the free wall may in turn detect reflected pressure waves received by the free wall. An acoustic module within the IMD may then determine a physiological condition of the patient, e.g., a bladder fullness state, based on the time delay between the transmitted and reflected pressure waves. In some examples in which the IMD also delivers stimulation therapy to the patient, e.g., incontinence therapy, the IMD may also automatically (Continued)

adjust stimulation therapy based on the determined physiological condition.

29 Claims, 10 Drawing Sheets

(51) Int. Cl.
*A61N 1/36* (2006.01)
*A61B 8/08* (2006.01)
*A61B 8/12* (2006.01)
*A61B 8/00* (2006.01)
*A61B 5/11* (2006.01)
*A61B 5/0488* (2006.01)

(52) U.S. Cl.
CPC ............ *A61B 5/205* (2013.01); *A61B 5/686* (2013.01); *A61B 5/7282* (2013.01); *A61B 5/74* (2013.01); *A61B 8/0858* (2013.01); *A61B 8/12* (2013.01); *A61B 8/5223* (2013.01); *A61B 8/56* (2013.01); *A61N 1/36007* (2013.01); *A61B 5/0031* (2013.01); *A61B 5/04882* (2013.01); *A61B 5/1107* (2013.01); *A61B 5/7455* (2013.01)

(56) References Cited

U.S. PATENT DOCUMENTS

| | | | |
|---|---|---|---|
| 5,156,157 A | 10/1992 | Valenta et al. | |
| 5,524,624 A * | 6/1996 | Tepper | A61B 8/582 600/439 |
| 6,579,247 B1 | 6/2003 | Abramovitch et al. | |
| 2001/0051766 A1 | 12/2001 | Gazdzinski | |
| 2003/0195415 A1 | 10/2003 | Iddan | |
| 2004/0204744 A1* | 10/2004 | Penner | A61B 5/0031 607/23 |
| 2005/0182342 A1 | 8/2005 | Dinsmoor et al. | |
| 2005/0216069 A1 | 9/2005 | Cohen et al. | |
| 2006/0009818 A1* | 1/2006 | Von Arx | A61B 5/0028 607/60 |
| 2007/0027494 A1 | 2/2007 | Gerber | |
| 2007/0027495 A1 | 2/2007 | Gerber | |
| 2007/0123778 A1 | 5/2007 | Kantorovich | |
| 2007/0255176 A1 | 11/2007 | Rondoni et al. | |
| 2011/0124955 A1 | 5/2011 | Ciquin et al. | |

FOREIGN PATENT DOCUMENTS

| | | |
|---|---|---|
| EP | 1911529 A1 | 4/2008 |
| FR | 2869521 A1 | 11/2005 |
| FR | 2920087 A1 | 2/2009 |
| WO | 8606606 A1 | 11/1986 |
| WO | 9733513 A1 | 9/1997 |
| WO | 2007137162 A2 | 11/2007 |
| WO | 2005114820 A2 | 4/2008 |

OTHER PUBLICATIONS

"The Principles of Medical Ultrasound", http://www.mrcophth.com/commonultrasoundcases/principlesofultrasound.html, Feb. 1, 2001, 6 pages.*
"Fundamentals of Ultrasound Imaging", http://dynamicultrasound.org/dugphysics.html, Mar. 11, 2007, 13 pages.*
"Medical Physics—Ultrasound", http://www.genesis.net.au/~ajs/projects/medical_physics/ultrasound/, Aug. 17, 2008, 6 pages.*
"Housing", www.merriam-webster.com/dictionary/housing, Apr. 25, 2016, 3 pages.*
Examination Report from Counterpart European Patent Application No. 12706129.9, dated May 22, 2014, 4 pp.
European Examination Report from counterpart Application No. 12706129.9-1657, dated Apr. 10, 2015, 6 pp.
International Search Report and Written Opinion of international application No. PCT/US2012/022388, dated May 23, 2012, 10 pp.
Examination Report from counterpart European Patent Application No. 12706129.9, dated Sep. 9, 2016, 4 pp.
Response to Examination Report dated Sep. 9, 2016, from counterpart European Application No. 12706129.9, filed Jan. 18, 2017, 9 pp.
Summons to Attend Oral Proceedings pursuant to Rule 115(1) EPC from European Patent Application No. 12706129.9, dated Mar. 5, 2018, 10 pp.
Notice of Intent to Grant and Text Intended to Grant from counterpart European Application No. 12706129.9, dated Nov. 5, 2018, 130 pp.
Response to Examination Report dated Apr. 24, 2017, from counterpart European Application No. 12706129.9, filed Sep. 4, 2017, 10 pp.
Communication pursuant to Article 94(3) EPC from counterpart European Application No. 12706129.9, dated Apr. 24, 2017, 6 pp.

* cited by examiner

PHYSIOLOGICAL CONDITION DETERMINATION BASED ON PRESSURE WAVE PRODUCED BY AN IMPLANTABLE MEDICAL DEVICE HOUSING

This application is a U.S. National Stage filing under 35 U.S.C. 371 of copending PCT Application Serial No. PCT/US2012/022388, filed Jan. 24, 2012, which claims the benefit of U.S. Provisional Application No. 61/437,299, filed Jan. 28, 2011, and entitled "PHYSIOLOGICAL CONDITION DETERMINATION BASED ON PRESSURE WAVE PRODUCED BY AN IMPLANTABLE MEDICAL DEVICE HOUSING."

TECHNICAL FIELD

The disclosure relates to implantable medical devices and, more particularly, medical devices that sense a physiological parameter of a patient.

BACKGROUND

Urinary disorders, such as an inability to control urinary function, are common problems afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging or illness. Example urinary disorders include, for example, urgency and frequency disorders, urge incontinence, stress incontinence, and urinary retention disorders. Urgency and frequency disorders may involve the feeling of impending urination without the actual voiding of urine. Retention and voiding dysfunctions, for example, may involve the loss of urine and be at least partially attributable to injury or disease (e.g., a spinal cord injury). Some patients suffering from injury or disease that affects bladder function may not be able to void or have reduced levels of sensation when the bladder is full. These disorders may result in kidney damage and other complications.

In some cases, a urinary disorder may be at least partially attributable to improper sphincter function, either in the internal urinary sphincter or external urinary sphincter. For example, aging may result in weakened sphincter muscles, which may cause incontinence. Some patients also may suffer from nerve disorders that prevent proper triggering and operation of the bladder or sphincter muscles.

Electrical stimulation of nerves in the pelvic floor may provide an effective therapy for a variety of urinary (and, in some cases, fecal) disorders, including retention and voiding dysfunctions. For example, an implantable neurostimulator may be provided to deliver electrical stimulation to the sacral nerve to induce sphincter constriction and thereby close or maintain closure of the urethra at the bladder neck.

SUMMARY

Devices, systems, and techniques for determining a physiological condition of a patient are described. In one example, an implantable medical device (IMD) produces and detects pressure waves with a portion of the IMD housing. The portion of the IMD housing may be a free wall that is configured to move (e.g., oscillate) to generate pressure waves that are transmitted into adjacent fluids or tissue within a body of a patient and detect the pressure waves that were transmitted through tissue or fluid within the body. An actuator element contacts the free wall to generate pressure waves, and a detector may contact the free wall to detect wall motion. Based on the relative position of anatomical structures and bodily fluids to the IMD housing, the IMD may determine a physiological condition of a patient.

In some examples, the determined physiological condition may be used to control therapy delivery to the patient. For example, the IMD may deliver electrical stimulation therapy to the patient. Because therapy needs may vary over time, e.g., based on the physiological condition of the patient, the IMD may adjust specific stimulation therapy parameters based on a determined physiological condition of the patient. In this manner, the IMD may deliver responsive therapy based on a physiological condition determined with the free wall of the IMD housing. In some examples in which the IMD is configured to deliver electrical stimulation therapy configured to manage urinary incontinence, the IMD may be implanted inferior to the bladder and lateral relative to the labia, with the free wall of the IMD housing facing the bladder. The IMD may include an acoustic module that monitors a bladder fullness state based on bladder walls location, which may be indicated by the pressure waves generated by a free wall of the IMD housing and reflected back to the acoustic module. In turn, the IMD may adjust stimulation therapy according to the bladder fullness state.

In one aspect, the disclosure is directed to a method that includes producing a pressure wave within a patient with a portion of a housing of an implantable medical device, wherein the housing substantially encloses a processor, detecting at least one reflected pressure wave with the housing portion, and automatically determining a physiological condition of the patient based on the at least one reflected pressure wave.

In another aspect, the disclosure is directed to a system that includes an implantable medical device comprising a device housing, an acoustic module configured to produce a pressure wave within a patient with a portion of the device housing and detect at least one reflected pressure wave with the housing portion, and a processor configured to automatically determine a physiological condition of the patient based on the at least one reflected pressure wave, wherein the device housing substantially encloses the processor.

In an additional aspect, the disclosure is directed to a system that includes means for producing a pressure wave within a patient with a portion of a housing of an implantable medical device, wherein the housing substantially encloses a processor, means for detecting at least one reflected pressure wave with the housing portion, and means for automatically determining a physiological condition of the patient based on the at least one reflected pressure wave.

In another aspect, the disclosure is directed to an article of manufacture comprising a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein. In some examples, the computer-readable medium may be non-transitory.

The details of one or more aspects of the disclosure are set forth in the accompanying drawings and the description below. Other features, objects, and advantages of the examples of the disclosure will be apparent from the description and drawings, and from the claims.

DETAILED DESCRIPTION

Figure 1:
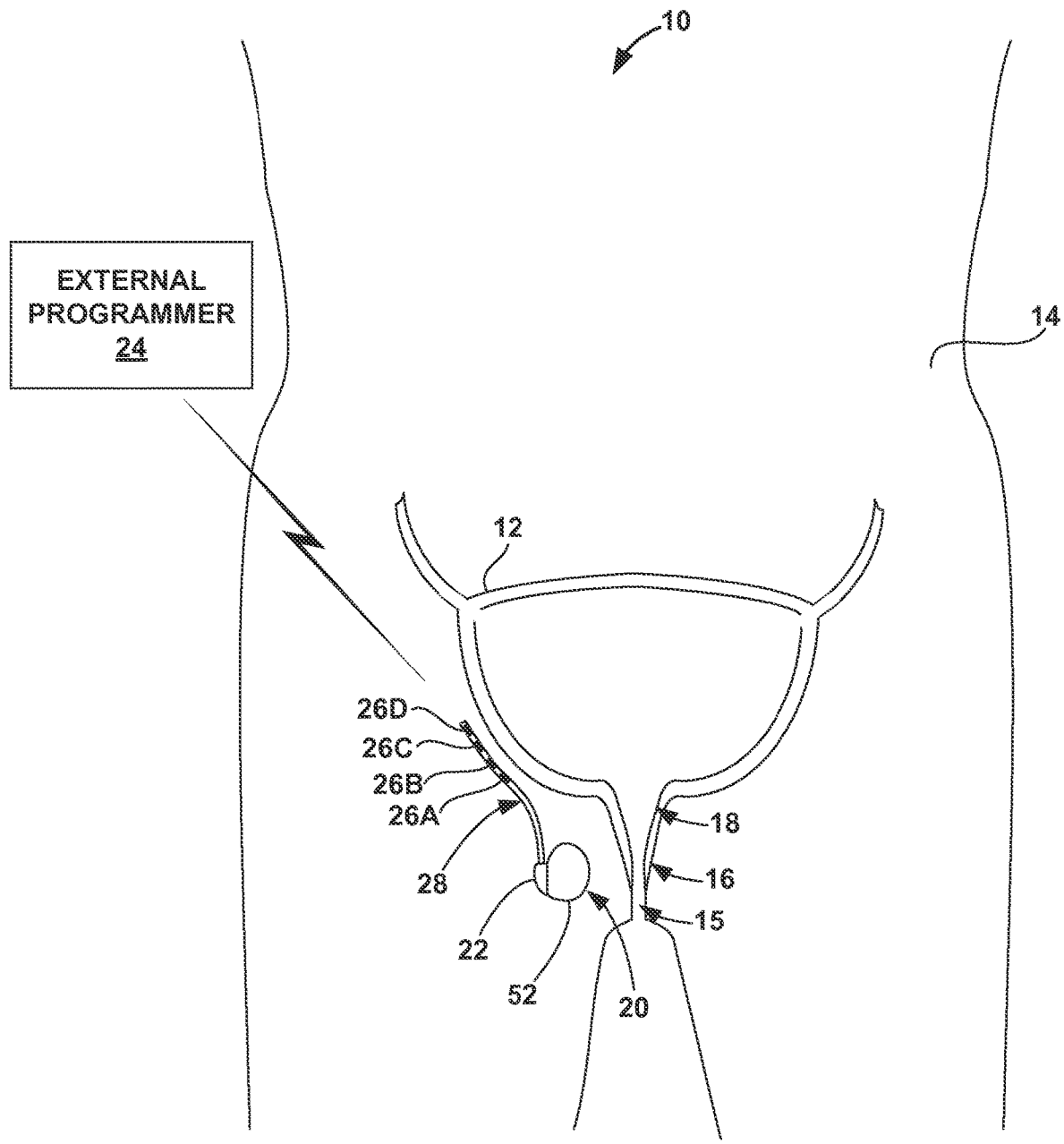
FIG. 1 is a conceptual diagram illustrating an example system that produces and detects pressure waves with a housing of an implantable medical device (IMD) to determine a bladder fullness state of a patient.

A physiological condition of a patient is determined based on a detection of pressure waves produced by at least a portion of a housing of an implantable medical device (IMD), transmitted through tissue and/or fluid within the patient's body, and reflected back to the housing. Some physiological conditions, e.g., anatomical structure changes, structure locations, and fluid flow, may be identified with pressure waves. Pressure waves are disturbances that transfer energy through a medium. In some examples, pressure waves may be classified as ultrasound waves, acoustic waves, or even infrasound waves depending upon the frequency of the waves. When the pressure wave travels from a first medium of one density to a second medium of another density, at least some of the pressure wave can be reflected and travel away from the second medium. Based on the timing and/or signature of the reflected pressure waves, it may be possible to identify anatomical structures and distances between anatomical structures, which may be indicative of specific physiological conditions. The pressure waves used herein to determine a physiological condition of a patient may be of any suitable frequency, e.g., ultrasonic or audible.

The IMD housing may be used to produce and detect the pressure waves within a patient. A portion of the IMD housing may be configured as a free wall capable of moving with respect to the rest of the IMD housing and with respect to at least some internal components. An actuator element may contact the free wall and move the free wall such that pressure waves are generated and transmitted into the patient. At least some of the energy of the transmitted pressure waves reflect off tissue or fluid interfaces within a patient and are reflected back to the IMD housing. A detector element in communication with the free wall may be configured to detect motion of the free wall caused by the reflected pressure waves. An acoustic module within the IMD may be configured to automatically determine the physiological condition of a patient based on the time delay or other signature of the reflected pressure waves. The IMD may perform this detection at predetermined interval or on demand. The IMD may also calibrate the acoustic module to levels or states of the physiological condition to previous detections or upon a patient input identifying an appropriate time for calibration. Although an acoustic module is generally described, the acoustic module may be configured to produce and detect pressure waves of any frequency (e.g., ultrasound, acoustic, or infrasound waves).

In addition to determining physiological conditions, the IMD may deliver stimulation therapy, e.g., electrical stimulation or drug therapy, to the patient. The IMD may use the determined physiological conditions for real-time, or less frequent but continuous, monitoring of the patient status and/or therapy efficacy. If a state of the physical condition surpasses a predetermined threshold, the IMD may adjust one or more stimulation parameters of the stimulation therapy to effectively treat the patient. However, the IMD may communicate the determined physiological conditions to other external or implanted devices that deliver therapy.

In one example, the IMD may deliver electrical stimulation therapy to treat urinary dysfunction disorders, e.g., incontinence, urgency, or retention disorders. The IMD may be implanted in any suitable location for detecting the physiological condition of the patient based on pressure waves generated by the IMD, as well as for delivering stimulation to the patient to treat the urinary incontinence. In some examples, the IMD is implanted at an interior location (e.g., within tissue of the patient), such as inferior of the bladder and lateral of the labia. With the free wall of the IMD housing directed towards the bladder, the acoustic module may use reflected pressure waves to determine a bladder fullness state of the patient's bladder. This determination may include identifying a change in bladder distance from the IMD or even a distance between proximal and distal walls of the bladder. As the volume of fluid within the bladder increases, the relative distance between the bladder and the IMD may decrease. In addition, as the volume of fluid within the bladder increases, the relative distance between opposing walls of the bladder may increase. The IMD may adjust stimulation therapy (e.g., activate stimulation therapy, increase the therapy delivery duty cycle, or increase an intensity of stimulation, which may be a function of stimulation parameters such as stimulation amplitude and frequency) as the bladder fullness state increases to prevent involuntary voiding by the patient. In some examples, the IMD may deactivate stimulation therapy, decrease the therapy delivery duty cycle, or decrease an intensity of stimulation as the bladder empties. This closed-loop feedback therapy system may provide more efficacious treatment and require less energy consumption when compared to an open-loop system.

In other examples, however, the bladder fullness state may merely be used to monitor the patient, e.g., as an objective measure of patient voiding based upon intermittent bladder fullness state monitoring. For example, the bladder fullness state determined based on the pressure signals can be used to generate a voiding diary that tracks the bladder fill cycle of the patient (e.g., the time from a relatively empty state to a relatively full state). An automated voiding diary may be useful in diagnosis of urological disorders. Rather than relying on patient input to generate the voiding diary, the techniques described herein for monitoring a bladder fullness state can be used to generate an automatic voiding diary, which may be less burdensome on the patient, and, in some examples, more accurate (e.g., less human error and less reliance on the patient to remember to record information about the bladder fullness). In some examples, the voiding diary may also be generated based the monitored bladder fullness state (or other physiological condition) when the IMD delivers stimulation therapy to the patient to manage urinary incontinence symptoms.

Instead of, or in addition to, detecting the bladder fullness state, pressure waves may be used to detect bladder contractions and/or bladder emptying. The pressure waves may be used to detect changes in the distance between bladder walls over time. Sudden change in bladder wall distances, or an increase or decrease in one or more dimensions of the bladder, may be indicative of a bladder contraction. When a threshold increase in bladder contraction frequency or intensity are detected or a threshold bladder contraction frequency is detected, an IMD may increase the stimulation intensity of electrical stimulation is delivered to the patient. If an emptying of the bladder is detected, IMD 14 may reduce the intensity of stimulation or suspend all stimulation therapy until the bladder fill level reaches a particular level (e.g., a predetermined threshold). In some examples, this bladder information may be used to create a bladder capacity or bladder voiding frequency log instead of, or in addition to, providing feedback for controlling the stimulation therapy.

Urinary incontinence refers to a medical condition in which a patient has an inability to control urinary function, and may include urge urinary incontinence, stress incontinence, or both stress and urge incontinence, which may be referred to as mixed urinary incontinence. Urge incontinence may also be referred to as overactive bladder or as leading to overactive bladder activities. Urinary incontinence may be an example of a urinary disorder. As used in this disclosure, the term "urinary disorders" may include disorders in which a loss of urine occurs when not desired, such as stress or urge incontinence, urinary urgency, urinary frequency, and disorders in which urination does not occur as desired, such as urinary retention disorder. Urinary disorders may be caused by age, illness, injury, disease, or combinations thereof. In cases where a patient has a loss of sensation of bladder fullness, detection of bladder volume or fullness may be at least partially effective in treating certain urinary disorders by providing artificial bladder fullness feedback.

One type of therapy for treating urinary disorders includes delivery of electrical stimulation. For example, delivery of electrical stimulation from an implantable medical device to one or more nerves innervating the pelvic floor, such as the sacral nerve, pudendal nerve, dorsal genital nerve, or branches of any of the aforementioned nerves, may provide an effective therapy for urinary disorders (e.g., may help prevent involuntary voiding events from occurring). For example, electrical stimulation of the sacral nerve may modulate afferent nerve activities to restore more normal urinary function. In this manner, electrical stimulation may be used to treat urgency and frequency disorders, urge incontinence, stress incontinence, and retention. Monitoring the bladder fullness state or other bladder conditions may be useful as feedback for stimulation therapy, to prevent kidney damage, providing biofeedback on when to void or catheterize the bladder, and other therapeutic purposes.

Although this disclosure may generally describe the use of an IMD for incontinence diagnosis and therapy, the techniques described herein may be used to determine any type of physiological condition and adjust a corresponding treatment. For example, the IMD may be used to detect a colon fullness state for fecal incontinence therapy, a stomach or intestine fullness state for gastrointestinal therapy, or any other condition or anatomical structure capable of detection with pressure waves.

FIG. 1 is a conceptual diagram illustrating example therapy system 10 that produces and detects pressure waves with a housing of implantable medical device (IMD) 20 to determine a bladder fullness state of patient 14. As shown in FIG. 1, therapy system 10 includes IMD 20, which is coupled to lead 28 via header 22 and in communication with external programmer 24. IMD 20 generally operates as a therapy device that delivers electrical stimulation to, for example, a pelvic floor nerve, a pelvic floor muscle, the urinary sphincter, the anal sphincter, or other pelvic floor targets. Pelvic floor nerves include peripheral nerves such as sacral nerves, pudendal nerves and associated branches, and dorsal genital nerves. IMD 20 provides electrical stimulation therapy to patient 14 by generating and delivering a programmable electrical stimulation signal (e.g., in the form of electrical pulses or a continuous time signal) to a target therapy site via lead 28 and, more particularly, via electrodes 26A-26D (collectively referred to as "electrodes 26") disposed proximate to a distal end of lead 28. In other examples, IMD 20 may not be configured to deliver stimulation therapy to patient 14, but may be used only for patient monitoring.

IMD 20 may monitor physiological conditions, e.g., a bladder fullness state of bladder 12 over an extended period of time. In addition, in some examples, IMD 20 may deliver electrical stimulation therapy over an extended, or chronic, period of time to patient 14. Generally, IMD 20 may deliver electrical signals, e.g., pulses or a continuous wave signal, according to a stimulation therapy program to treat patient 14. In the example of FIG. 1, IMD 20 may deliver therapy to treat patient 14 for urinary disorders. The therapy program may define a set of therapy parameters that define the electrical stimulation, e.g., pulse rate, pulse width, voltage or current amplitude, and pulse frequency. In some examples, IMD 20 may also provide a secondary electrical stimulation therapy to provide additional therapeutic support. This secondary electrical stimulation therapy may be delivered in place of or in addition to the regular chronic therapy, and the second electrical stimulation therapy may be provided in response to the determined physiological condition or a request from the patient. In the context of incontinence therapy, the secondary electrical stimulation therapy may be provided as a "boost" of additional therapy when patient 14 senses that a voiding event is imminent.

IMD 20 may deliver drug therapy in addition to or in place of the electrical stimulation therapy. For example, IMD 20 may deliver electrical stimulation therapy to treat urinary disorders of patient 14 while also delivering drug therapy when needed to prevent unwanted voiding of bladder 12. In other examples, IMD 20 may be a drug pump that periodically delivers a bolus of drug adjacent to pelvic floor muscles and/or pelvic floor nerves to reduce unwanted voiding events from bladder 12.

Stimulation therapy may be provided by IMD 20 directly to pelvic floor nerves or muscles such as internal urinary sphincter 18, external urinary sphincter 16, or periurethral muscles (not shown). In some cases, it is undesirable for the external urinary sphincter or periurethral muscles to always remain closed during stimulation therapy. However, sphincter closure may help prevent the involuntary leakage of urine from bladder 12. Thus, the short-term closure of sphincter provided by a second electrical stimulation therapy (which can also be referred to as a "boost" of therapy) delivered by IMD 20 may prevent the occurrence of involuntary voiding events during the occurrence of acute bladder contractions.

In the example of FIG. 1, IMD 20 delivers stimulation therapy to patient 14 via electrodes 26 on lead 28. The target therapy sites for the stimulation therapy may be different fibers of the same nerve. In other examples, electrodes 26 may deliver stimulation therapy to different target stimulation sites. For example, IMD 20 may deliver stimulation therapy to a sacral nerve of patient 14 to relax bladder 12 and deliver stimulation therapy to a hypogastric nerve to help maintain contraction or help induce contraction of the internal urinary sphincter 18 and external urinary sphincter 16 or periurethral muscles, a pudendal nerve, a dorsal penile nerve in a male patient or a dorsal clitoral nerve in a female patient to help maintain or help induce contraction of the external urinary sphincter 16, periurethral muscles, internal urinary sphincter 18, or any combination thereof. In other examples, IMD 20 may deliver the stimulation therapy to a hypogastric nerve of patient 14 to help close or help maintain internal urinary sphincter closure or urethral tone.

IMD 20 may be surgically implanted in patient 14 at any suitable location within patient 14 that also allows a physiological condition to be determined by producing pressure waves via at least a portion of the outer housing of IMD 20 and detecting the pressure waves via a detector coupled to the outer housing (e.g., substantially enclosed within the outer housing or mechanically attached to an outer surface of the outer housing). To aid in the monitoring of the physiological condition of patient 14 (e.g., a bladder fullness state) via pressure waves, IMD 20 may be implanted such that only soft tissues or fluid is disposed between IMD 20 and bladder 12 (or other tissue or fluid that is to be monitored by therapy system 10). Dense materials, e.g., bones, may limit the ability of IMD 20 to transmit pressure waves to bladder 12 and detect pressure waves within patient 14 because the dense materials may interfere with (e.g., block or dampen) the transmission of pressure waves from IMD 20 to the monitored tissue or fluid site within patient 14. In some examples, as shown in FIG. 1, IMD 20 may be located at an internal location inferior to bladder 12 and lateral to a labia for pressure waves to travel between IMD 20 and bladder 12. In other examples, IMD 20 may be implanted in the abdomen of patient 14 to avoid pressure wave interference from pelvic bones. Although IMD 20 may be implanted at any location within patient 14, IMD 20 may generally be located in proximity to the tissue or fluid that is desired to be monitored by IMD 20.

IMD 20 includes biocompatible outer housing 52, which may be formed from titanium, stainless steel, a liquid crystal polymer, or another biocompatible material. The proximal end of lead 28 is both electrically and mechanically coupled to IMD 20, either directly or indirectly, e.g., via a respective lead extension. Electrical conductors disposed within the lead body of lead 28 may electrically connect stimulation electrodes, such as electrodes 26, to a therapy delivery module (e.g., a stimulation generator) within IMD 20. In other examples, additional leads may be coupled to IMD 20 and carry additional stimulation electrodes or sensing electrodes.

One or more medical leads, e.g., lead 28, may be connected to IMD 20 and surgically or percutaneously tunneled to place one or more electrodes carried by a distal end of the respective lead at a desired pelvic nerve or muscle site, e.g., one of the previously listed target therapy sites such as a sacral or pudendal nerve. For example, lead 28 may be positioned such that electrodes 26 deliver stimulation therapy to a sacral or pudendal nerve to relax bladder 12 and/or deliver stimulation therapy to hypogastric nerve, a pudendal nerve, a dorsal penile/clitoral nerve, the urinary sphincter, or any combination thereof to a promote closure of a urinary sphincter of patient 14. Electrodes 26 of the common lead 28 may deliver stimulation to the same or different nerves. In other examples of therapy system 10, IMD 20 may be coupled to more than one lead that includes electrodes for delivery of electrical stimulation to different stimulation sites within patient 14, e.g., to target different nerves.

In the example shown in FIG. 1, lead 28 is cylindrical. Electrodes 26 of lead 28 may be ring electrodes, segmented electrodes or partial ring electrodes. Segmented and partial ring electrodes each extend along an arc less than 360 degrees (e.g., 90-120 degrees) around the outer perimeter of lead 28. In examples, leads 28 may be, at least in part, paddle-shaped (i.e., a "paddle" lead). In some examples, segmented or partial ring electrodes 26 of lead 28 may be useful for targeting different fibers of the same or different nerves to generate different physiological effects for the first and second stimulation therapies. As described in further detail below, segmented electrodes may be useful for delivering relatively high frequency stimulation (e.g., about 66 Hertz) and relatively low frequency stimulation (e.g., about 15 Hertz) to activate both fast twitch muscles and low twitch muscles substantially simultaneously or at alternating time slots.

The illustrated numbers and configurations of lead 28 and electrodes 26 carried by lead 28 are merely one example. Other configurations, i.e., number and position of leads and electrodes are possible. For example, in other examples, IMD 20 may be coupled to additional leads or lead segments having one or more electrodes positioned at different locations in the pelvic region of patient 14. The additional leads may be used for delivering different stimulation therapies to respective stimulation sites within patient 14 or for monitoring physiological parameters of patient 14. As an example, in an example in which the target therapy sites for multiple stimulation therapies are different, IMD 20 may be coupled to two or more leads, e.g., for bilateral or multilateral stimulation.

As previously indicated, IMD 20 generates and delivers electrical stimulation therapy to a patient to manage urinary or fecal incontinence and, in some examples, an additional electrical stimulation therapy ("second" electrical stimulation therapy) to provide an additional boost of therapy that generates a second physiological effect to help further manage urinary or fecal incontinence. In some examples, IMD 20 controls the delivery of the second electrical stimulation therapy to patient 14 based on input received from patient 14 or a physiological condition, e.g., a bladder fullness state, determined by reflected pressure waves detected by a portion of the IMD housing. As one example, IMD 20 may deliver a second stimulation therapy in response to detecting a bladder fullness state exceeding a predetermined threshold indicative of imminent urine leakage. In another example, IMD 20 may determined, based on pressure wave produced by housing 52 and subsequently detected by housing 52, that fluid is flowing out of urethra 15 and additional stimulation therapy is necessary to prevent further fluid flow.

As described in further detail below, a portion of housing 52 of IMD 20 is used to determine a physiological condition of patient 14. The physiological condition may be a bladder fullness state as shown in FIG. 1, or the physiological condition may be a bladder contraction frequency, a colon fullness state, a stomach or intestine fullness state, or even a urine or fecal flow state. Generally, the physiological condition may be any condition within patient 14 detectable by the detection of reflected pressure waves with a portion of housing 52, where the pressure waves are generated with a portion of housing 52 and transmitted through tissue and/or bodily fluids of patient 14. In this manner, IMD 20 may generate pressure waves of any frequency allowable by the physical parameters of the portion of housing 52 and reflectable by tissue and/or bodily fluid within patient 14. For example, the pressure waves may be ultrasound waves above 20,000 Hz, acoustic waves between 20 Hz and 20,000 Hz, or even infrasound waves less than 20 Hz.

Although not shown in FIG. 1, the portion of housing 52 used to produce and detect pressure waves may be positioned such that the portion, or free wall, is facing the anatomical structures of interest. An anatomical structure of interest may be any structure (e.g., comprised of tissue and/or bodily fluids, and not necessarily limited to organs, muscles, and the like) within patient 14 that is detected or imaged with the produced pressure waves from housing 52. For example, if a bladder fullness state is being determined, the portion of housing 52 used to produce and detect pressure waves may be positioned to face bladder 12. In some examples, the portion of housing 52 used to produce and detect pressure waves includes a free wall of the outer housing of IMD 20, where the free wall may be substantially flat, but, in other examples, can also be or include a curved free wall. The free wall of housing 52 may be constructed of a desired thickness and surface area to tune the free wall to desired frequencies of the pressure waves. The free wall may be tuned according to the desired anatomical structures and fluids detected by the pressure waves.

In some examples, housing 52 may have two or more portions that are configured to produce and transmit pressure waves and/or detect the pressure waves generated by the two or more portions and transmitted through and/or reflected by tissue and/or a fluid within patient 14. For example, a first portion of housing 52 may be tuned to produce and detect pressure waves of a certain frequency designed to target a more proximal tissue site, e.g. a proximal bladder wall, and a second portion of housing 52 may be tuned to produce and detect pressure waves of a different frequency designed to target a more distal tissue site, e.g. a distal bladder wall. In other examples, a first portion of housing 52 may be tuned to produce and transmit pressure waves into patient 14 and a second portion of housing 52 may be tuned to detect the pressure waves transmitted through and/or reflected by from anatomical structures or bodily fluids. In any case, the housing 52 of IMD 20 is used to produce pressure waves transmitted into patient 14 and detect (e.g., receive) reflected pressure waves originating from one or more anatomical structures within patient 14 in response to contact by the housing 52 produced pressure waves. In other words, reflected waves may be the result of produced pressure waves contacting one or more anatomical structures.

System 10 may also include an external programmer 24, as shown in FIG. 1. In some examples, programmer 24 may be a wearable communication device, handheld computing device, computer workstation, or networked computing device. Programmer 24 may include a user interface that receives input from a user (e.g., patient 14, a patient caretaker, or a clinician). The user interface may include, for example, a keypad and/or a display for receiving user input, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 and/or IMD 20 remotely via a networked computing device.

Patient 14 may interact with programmer 24 to control IMD 20 to deliver the stimulation therapy, to manually abort the delivery of stimulation therapy by IMD 20, or to inhibit the delivery of stimulation therapy by IMD 20, e.g., during voluntary voiding events. Patient 14 may, for example, use a keypad or touch screen of programmer 24 to cause IMD 20 to deliver the second, or additional, stimulation therapy, such as when patient 14 senses that a leaking episode may be imminent. In this way, patient 14 may use programmer 24 to control the delivery of the second stimulation therapy "on demand," e.g., when an extra boost of the stimulation therapy is desirable.

Patient 14 (or a patient caretaker or clinician) may also interact with programmer 24 to monitor the physiological condition determined by IMD 20. For example, programmer 24 may generate a notification that indicates the current bladder fullness state determined by detecting reflected pressure waves from bladder 12. Programmer 24 may indicate the bladder fullness state via a visible message, audible alert, or somatosensory alert (e.g., vibration). Patient 14 may anticipate and plan ahead for future voiding events by monitoring an objective indication of bladder fullness provided by programmer 24. In addition, patient 14 may instruct programmer 24 to calibrate the determination of the bladder fullness state by IMD 20 if the bladder fullness state indicated by programmer 24 is no longer similar to the bladder fullness state perceived by patient 14. By allowing patient 14, or another health care provider, to monitor the physiological condition, the efficacy of therapy may be improved with or without changes to stimulation therapy.

In some examples, patient 14 may interact with IMD 20 (e.g., via programmer 24 or directly via IMD 20) to control IMD 20 to deliver the stimulation therapy, manually abort the delivery of stimulation therapy, or inhibit the delivery of stimulation therapy. In such examples, a motion sensor is integrated in IMD 20 that is responsive to patient 14 tapping IMD 20 through the skin. The number, rate, or pattern of taps may be associated with the different programming capabilities. In this way, patient 14 may be able to directly control delivery of therapy in the event that programmer 24 is not within reach of patient 14.

A user, such as a physician, technician, surgeon, electrophysiologist, or other clinician, may also interact with programmer 24 or another separate programmer (not shown), such as a clinician programmer to communicate with IMD 20. Such a user may interact with programmer 24 to retrieve physiological or diagnostic information from IMD 20. The user may also interact with a programmer to program IMD 20, e.g., select values for the stimulation parameter values with which IMD 20 generates and delivers stimulation and/or the other operational parameters of IMD 20. For example, the user may use a programmer to retrieve information from IMD 20 regarding the contraction of bladder 12 and voiding events or other physiological conditions determined by IMD 20. As another example, the user may use a programmer to retrieve information from IMD 20 regarding the performance or integrity of IMD 20 or other components of system 10, such as lead 28 or a power source of IMD 20. In some examples, this information may be presented to the user as an alert if a system condition that may affect the efficacy of therapy is detected.

IMD 20 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 20 implant site in order to improve the quality or security of communication between IMD 20 and programmer 24.

Figure 2A:
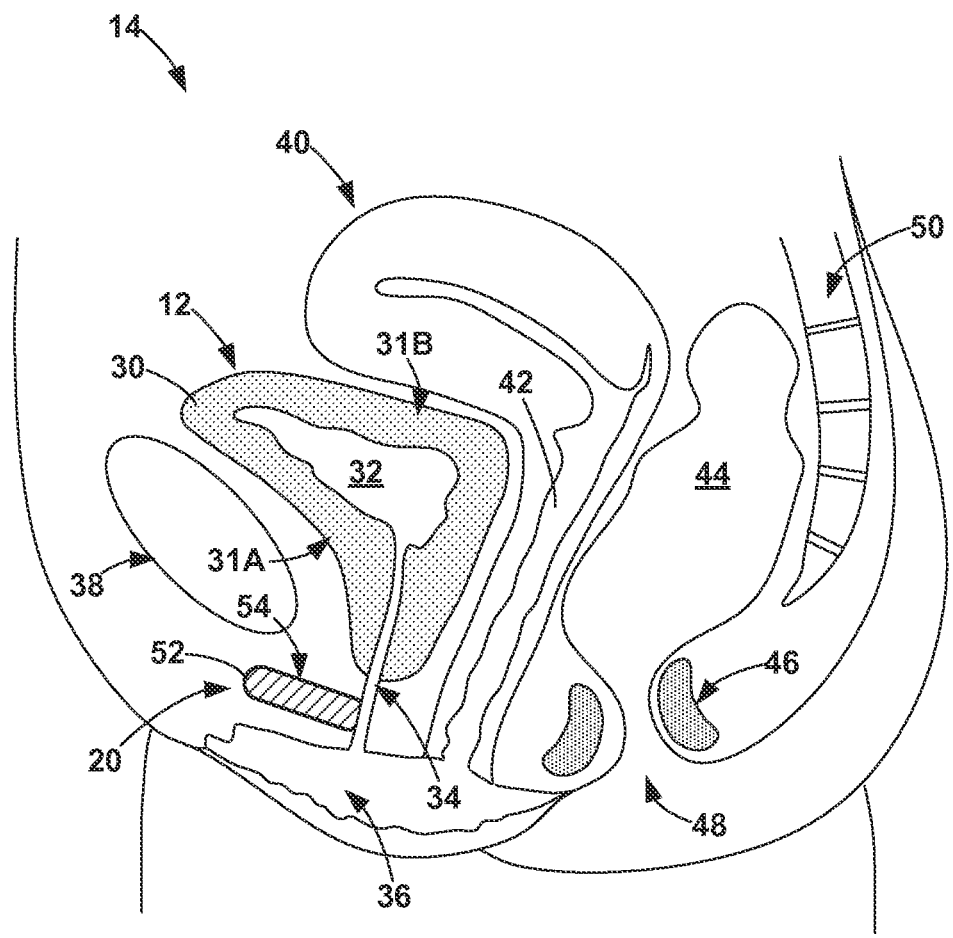
FIGS. 2A and 2B are conceptual diagrams illustrating example implant locations for the IMD of FIG. 1.
Figure 2B:
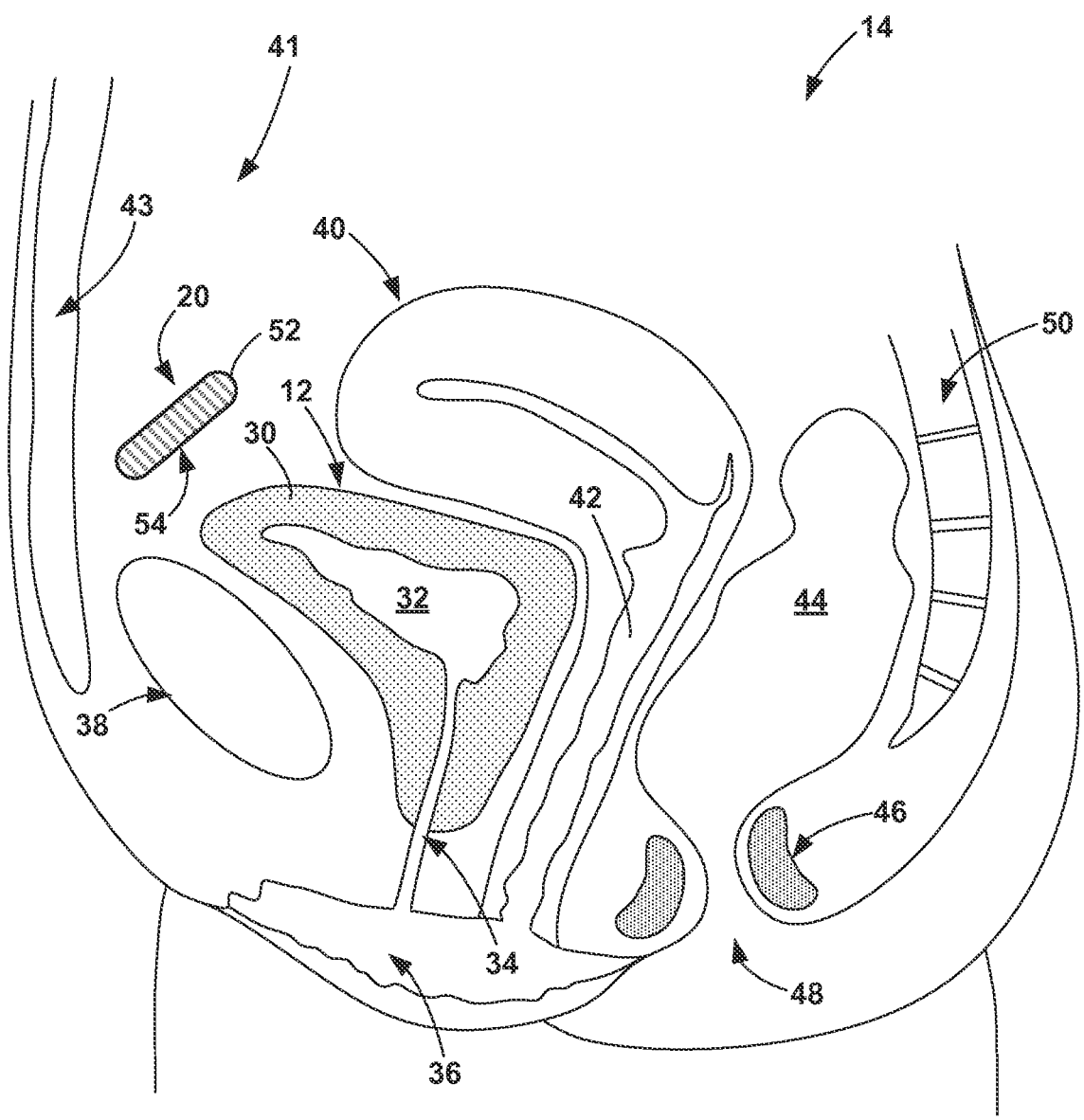

FIGS. 2A and 2B are conceptual diagrams illustrating example implant locations for IMD 20 of FIG. 1. FIG. 2A indicates representative anatomical structures within a cross-section of the pelvic region of a female patient 14. Patient 14 includes bladder 12, bladder wall 30, bladder cavity 32, urethra 34, labia 36, pelvic bone 38, uterus 40, vagina 42, colon 44, anal sphincter 46, anus 48, and sacrum 50. As shown in FIG. 2A, IMD 20 is positioned substantially inferior to bladder 12 and substantially lateral to labia 36 at an internal location within patient 14. This position of IMD 20 is adjacent to urethra 34 because IMD 20 offset from the midline of patient 14.

IMD 20 also includes outer housing 52 and free wall 54. As described herein, housing 52 is the outer housing of IMD 20 and substantially encloses operational circuitry of IMD 20, such as a processor, a memory, a therapy delivery module, a telemetry module, an acoustic module, sensors, and/or a power source. A portion of housing 52 defines free wall 54. In some examples, free wall 54 is not physically separated from the rest of housing 52, e.g., free wall 54 may be seamlessly integrated into the entire housing 52 or may be coupled to the rest of housing 52. Although free wall 54 may be physically different from the rest of housing 54 in some examples, free wall 54 is still a portion of housing 52 that encloses operational circuitry of IMD 20 and separates the internal IMD 20 components from patient 14 or another external environment and contaminants. For example, one side of free wall 54 may define an exterior surface of housing 52. As another example, one side of free wall 54 may face components inside housing 52. In other examples, free wall 54 is physically separate from the rest of housing 52 and mechanically connected thereto, e.g., in a manner that utilizes free wall 54 to define a part of housing 52.

IMD 20 may be positioned within patient 14 such that free wall 54 is facing the anatomical structure or structures to be interrogated by pressure waves produced from free wall 54. In other words, in examples in which free wall 54 is substantially planar, a plane of free wall may be orthogonal, or perpendicular, to the direction of the desired anatomical structures. In the example of FIG. 2A, free wall 54 is positioned such that produced pressure waves are directed to bladder wall 30 of bladder 12. IMD 20 is also positioned such that pelvic bone 38 does not substantially interfere with pressure waves travelling between free wall 54 and bladder wall 30. In this manner, pressure waves transmitted by free wall 54 may travel through soft tissues and fluid toward bladder wall 30, and at least some of the pressure waves reflected by bladder wall 30 may travel back through soft tissues toward free wall 54, which can also be used to detect the reflected pressure waves.

IMD 20 may determine the physiological condition of a bladder fullness state using IMD 20 positioned as shown in FIG. 2A. In one example, pressure waves produced by free wall 54 and reflected by bladder wall 30 may indicate the changing location of the proximal portion of bladder wall 30 with respect to free wall 54. As urine fills bladder cavity 32, bladder wall 30 will expand and push the proximal portion of bladder wall 30 closer to free wall 54. Because bladder wall 30 will be closer to free wall 54 as bladder 12 increases in volume, reflected pressure waves may take less time to return to free wall 54. Therefore, in some examples, the bladder fullness state is a function of the distance between free wall 54 and the proximal portion of bladder wall 30 (e.g., a shorter distance between free wall 54 and the proximal portion of bladder wall 30 detected by shorter return times for reflected pressure waves may indicate a larger bladder 12).

In another example, IMD 20 may determine the bladder fullness state by locating proximal portion 31A and distal portion 31B of bladder wall 30, where proximal portion 31A and distal portion 31B are determined relative to the location of free wall 54. Pressure waves produced by free wall 54 may induce reflected pressure waves from both proximal portion 31A of bladder wall 30 and distal portion 31B of bladder wall 30 through bladder cavity 32. That is, pressure waves produced by free wall 54 may reflect off of both proximal portion 31A of bladder wall 30 and distal portion 31B of bladder wall 30 through bladder cavity 32. The transmitted pressure waves from free wall 54 may first contact proximal portion 31A of bladder wall 30 and these first reflected pressure waves will return to free wall 54 quickly. After the transmitted pressure waves travel through the urine within bladder cavity 32, second reflected pressure waves may also be reflected by distal portion 31B of bladder wall 30. Based on the time delay between the first reflected pressure waves and the second reflected pressure waves to reach free wall 54, IMD 20 may determine a volume of bladder 12 and, accordingly, determine a bladder fullness state.

Although multiple transmitted and reflected pressure waves are described herein, in some examples, only one, or one set of, pressure waves may be transmitted by IMD 20 to determine a physiological condition of patient 14. In other examples, IMD 20 can transmit a plurality of pressure waves or a plurality of sets of pressure waves, and determine the physiological condition of patient 14 based on only one or one set of pressure waves. Although time differences between pressure waves from free wall 54 of housing 52 and reflected pressure waves are generally used herein for detecting one or more structures, reflected pressure waves of modulated frequencies and/or amplitude may be used to differentiate between different structures (e.g., proximal portion 31B and distal portion 31B of bladder 12) in other examples. In addition, the time delay between produced pressure waves and reflected pressure waves can be dependent upon the properties of the tissue and fluids through which the waves travel. In other words, the speed of pressure wave propagation can be dependent upon the tissue or fluid medium in which the pressure wave travels. Therefore, these properties of the tissues and fluids through which the pressure waves travel may be used to determine distances between anatomical structures or between IMD 20 and an anatomical structure.

In other examples, IMD 20 may be rotated such that free wall 54 generally faces urethra 34. Based on the detection of pressure waves produced by IMD 20 using free wall 54 and reflected by tissue of patient 14, IMD 20 may be capable of determining the rate of urine flow, if any, out of urethra 34. This urine flow may be used to determine a voiding status for patient 14. In some examples, pressure waves with higher frequencies, e.g., ultrasound frequencies, may be used for flow monitoring, e.g., in order to detect fluid flow within urethra 34 with free wall 54. In other examples, housing 52 may include multiple portions, or free walls, to determine multiple physiological conditions substantially simultaneously or at different times.

In other examples, free wall 54 may be used to determine two or more physiological conditions simultaneously. For example, depending on the frequency of produced pressure waves and parameters of free wall 54 (e.g., thickness, stiffness, or elasticity), IMD 20 may be capable of identifying multiple different reflected pressure wave frequencies and/or amplitudes from several different anatomical structures or fluids. These differing reflected pressure waves may be originated from single frequency pressure waves or produced pressure waves of differing frequencies. For example, IMD 20 may be capable of determining a bladder fullness state, a voiding status, and even a uterus condition of patient 14. In this manner, the physiological condition determination described herein is not limited to a single condition from one position of IMD 20.

FIG. 2B provides another example implant location and orientation for IMD 20 at an internal location within patient 14. IMD 20 is implanted within abdomen 41 and internal of abdominal muscles 43 such that free wall 54 of housing 52 substantially faces bladder wall 30 of bladder 12. In this position, IMD 20 may be able to use pressure waves to determine a bladder fullness state of bladder 12. With IMD 20 being internal of abdominal muscles 43, pressure waves may more easily travel between free wall 54 and bladder wall 30. Although IMD 20 may be external of abdominal muscles 43, the muscles may reduce the ability for pressure waves to travel between free wall 54 and the desired anatomical structures because muscles between free wall 54 and the target structure may attenuate or completely prevent the transmission of pressure waves.

In any of these examples or other examples, IMD 20 may be implanted within a pocket created by a surgeon and remain in place with free wall 54 correctly positioned. However, IMD 20 may require one or more anchors for free wall 54 to remain correctly oriented within patient 14 after implantation. Any suitable anchoring mechanism can be used. For example, one or more sutures may be used to anchor IMD 20 to surrounding tissue. In addition to or instead of the sutures, IMD 20 may include one or more mechanical anchors (e.g., tines, barbs, balloons, adhesive, and the like) attached to or part of housing 52 that engages with surrounding tissue to substantially fix IMD 20 in place and in a particular orientation. In some examples, the anchoring mechanism can be configured to encourage tissue in-growth. In some examples, IMD 20 may include an accelerometer or another sensor that may detect if IMD 20 has shifted orientations during therapy.

In other examples, IMD 20 may be implanted at various locations within patient 14 to monitor and determine physiological conditions in addition to or instead of the conditions discussed herein. For example, IMD 20 be positioned adjacent to colon 44 with free wall 54 oriented substantially towards colon 44. In this orientation, IMD 20 may generate pressure waves with free wall 54, transmit the pressure waves toward colon 44, and detect at least some of the pressure waves reflected by colon 44 to determine a colon fullness state. A colon fullness state may be useful for monitoring fecal incontinence patients. In some examples, IMD 20 may be positioned within patient 14 to monitor a condition or status of uterus 40, the stomach, a portion of the small or large intestine, or even abnormal/cancerous growth or atrophy of tissue. Therefore, the techniques for determining physiological conditions with free wall 54 are not limited to any particular condition, anatomical structure, or location within patient 14.

Although patient 14 has been described as female in the examples of FIGS. 2A and 2B, patient 14 may be male in other examples. IMD 20 may be positioned within any anatomical space for the determination of physiological conditions using produced and detected pressure waves with a portion of housing 52.

Figure 3:
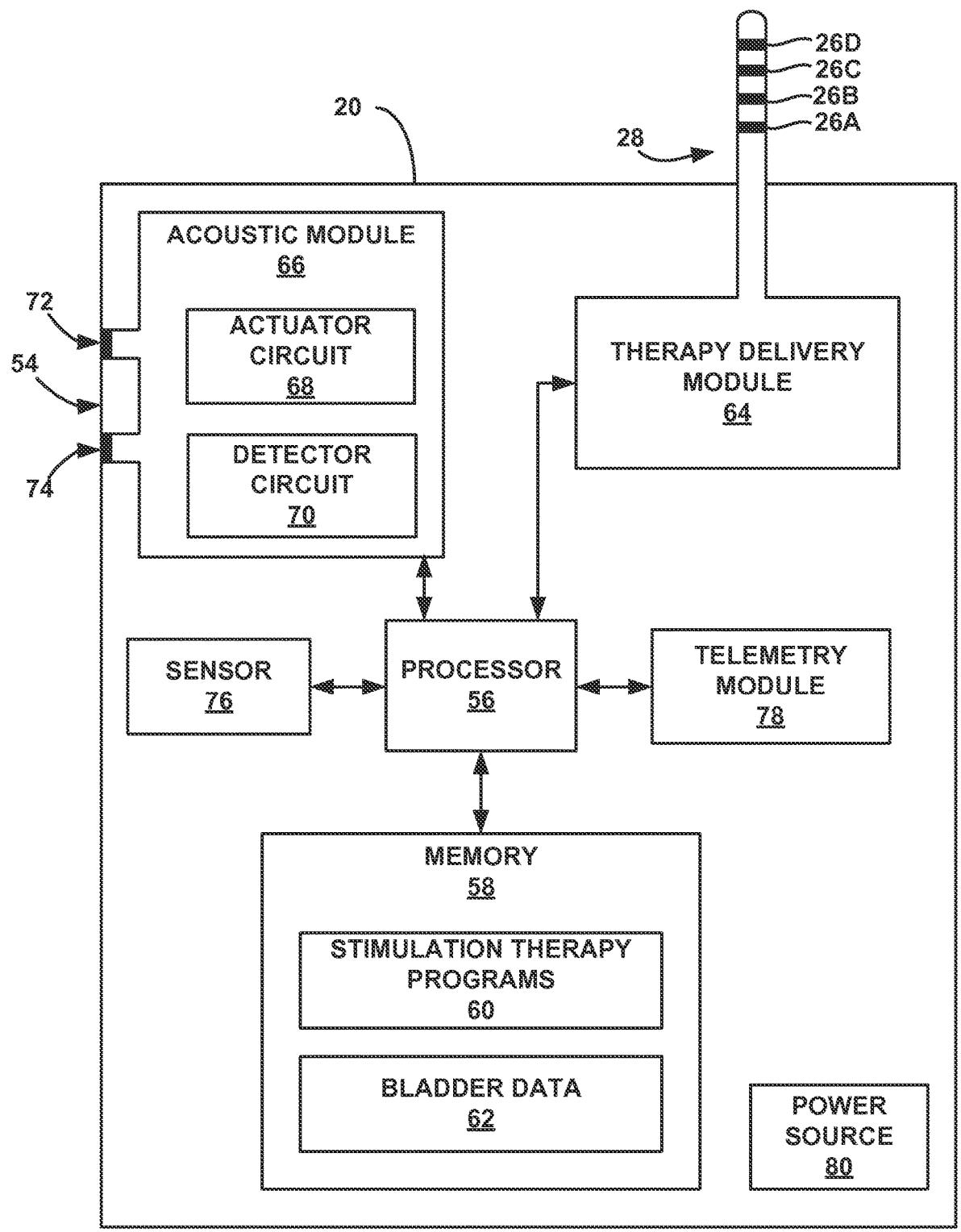
FIG. 3 is a block diagram illustrating an example configuration of the implantable medical device (IMD) of the systems shown in FIGS. 1 and 2.

FIG. 3 is a block diagram illustrating example components of IMD 20. In the example of FIG. 3, IMD 20 includes processor 56, memory 58, therapy delivery module 64, acoustic module 66, sensor 76, telemetry module 78, and power source 80. In the example shown in FIG. 3, memory 58 stores stimulation therapy programs 60 that specify stimulation parameters for the one or more stimulation therapies delivered to patient 14 by IMD 20. Memory 58 also stores bladder data 62, which processor 56 may use for controlling the timing of the delivery of the stimulation therapy or which may be stored for later analysis by a clinician (e.g. the bladder data 62 may be a part of a voiding diary). For example, bladder data 62 may include threshold values for a bladder fullness status, past bladder fullness states, past voiding events, or any other physiological data related to treating urinary disorders.

Therapy delivery module 64 is configured to generate and deliver therapy (e.g., stimulation signals) under the control of processor 56. In some examples, processor 56 controls therapy delivery module 64 by accessing memory 58 for selectively accessing and loading stimulation therapy programs 60 to therapy delivery module 64. Consistent with the techniques described in this disclosure, processor 56 may load one of stimulation therapy programs 60 to therapy delivery module 64 based on input received from acoustic module 66, sensor 76, or an indication of patient input received from another device and transmitted to IMD 20 via telemetry module 78.

By way of example, processor 56 may access memory 58 to load one of stimulation therapy programs 60 to therapy delivery module 64 for delivering stimulation therapy to patient 14. A clinician or patient 14 may select a particular program from stimulation therapy programs 60 from a list using a programming device, such as programmer 24 or a clinician programmer. Processor 56 may receive the selection via telemetry module 78. Therapy delivery module 64 delivers the selected stimulation therapy to patient 14 according to the selected program for an extended period of time, such as hours, days, weeks, or until patient 14 or a clinician manually stops or changes the program. The selected one of stimulation therapy programs 60 may define a schedule or an "on cycle" and "off cycle" duration for the stimulation therapy, such that a stimulation signal is not continuously delivered to patient 14, but periodically delivered in accordance with predetermined parameters for the first stimulation therapy.

In some examples, processor 56 may access memory 58 to load a second or additional stimulation therapy program from stimulation therapy programs 60 when prompted by a user via programmer 24 or the physiological condition determined by processor 56 using acoustic module 66 and/or sensor 76. Therapy delivery module 64 may then deliver the second stimulation therapy according to the second or additional stimulation therapy program until the second stimulation therapy is no longer desired or needed, e.g., as determined by processor 56. For example, the additional stimulation therapy program may time out after a predetermined period of time, a user may indicate that it is no longer needed, or acoustic module 66 may indicate that the physiological condition has changed.

Therapy delivery module 64 is configured to generate and deliver therapy, e.g., electrical stimulation in the example shown in FIG. 3, according to stimulation parameters, such as voltage or current amplitude, pulse rate (frequency), and pulse width specified by therapy programs, such as stimulation therapy programs 60. In some examples, therapy delivery module 64 delivers therapy in the form of electrical pulses. In other examples, therapy delivery module 64 delivers electrical stimulation in the form of continuous waveforms.

In some examples, the stimulation parameters for stimulation therapy programs 60 may be selected to relax bladder 12 (FIG. 1) or close or maintain internal urinary sphincter closure or urethral tone. An example range of stimulation parameters for the first stimulation therapy that may be effective in treating incontinence, e.g., when applied to the sacral or pudendal nerves, are as follows:

1. Frequency: between approximately 0.5 Hz and approximately 500 Hz, such as between approximately 10 Hz and approximately 250 Hz, or between approximately 10 Hz and approximately 25 Hz.

2. Amplitude: between approximately 0.1 volts and approximately 50 volts, such as between approximately 0.5 volts and approximately 20 volts, or between approximately 1 volt and approximately 10 volts.

3. Pulse Width: between approximately 10 microseconds ($\mu$s) and approximately 5000 $\mu$s, such as between approximately 100 $\mu$s and approximately 1000 $\mu$s, or between approximately 180 $\mu$s and approximately 450 $\mu$s.

In other examples, the stimulation parameters defined by one or more of stimulation therapy programs 60 may be generally different than those of other programs stored in memory 58. For example, stimulation parameter values may be configured to maximize closure of one or more of internal urinary sphincter, external urinary sphincter, and periurethral muscles. Stimulation parameter values may also be selected to minimize muscle fatigue. Muscle fatigue may occur when the force-generating ability of a muscle decreases as a result of the electrical stimulation.

An example range of stimulation pulse parameters for the second stimulation therapy programs are as follows:

1. Frequency: between approximately 15 Hz to approximately 30 Hz to activate slow-twitch muscles to minimize muscle fatigue while providing some sphincter closure, and between approximately 30 Hz and approximately 66 Hz to activate fast-twitch muscles, which may maximize sphincter closure.

2. Amplitude: approximately 2-4 times rheobase for the target nerve or muscle, such as about 0.5 volts to about 50 volts, or about 0.5 volts to about 10 volts, or about 4 volts to about 8 volts. Rheobase is the minimal electric current of infinite duration that results in an action potential or muscle twitch.

3. Pulse Width: between about 100 microseconds ($\mu$s) and about 1,000 $\mu$s.

In some examples, at least one of stimulation therapy programs 60 may include more than one set of stimulation parameters. In such examples, one set of stimulation parameters may be designed to activate fast-twitch muscle fibers in order to maximize closure of the urinary sphincter and/or periurethral muscles, and another set of stimulation parameters may be designed to activate slow-twitch muscle fibers in order to maintain closure of the urinary sphincter and/or periurethral muscles while minimizing muscle fatigue. The fast-twitch and slow-twitch muscle fibers may be selectively activated by activating specific nerve fibers with the same electrodes of a common lead, or different electrodes of a common lead (e.g., segmented electrodes specifically selected to target particular nerve fibers) or electrodes of separate leads or microstimulators.

As an example, in accordance with one of the stimulation therapy programs 60, IMD 20 may generate and deliver stimulation pulses having a relatively high frequency (e.g., about 66 Hz) for the first five seconds of the therapy interval to activate fast-twitch muscle fibers, and subsequently generate and deliver stimulation pulses at a lower relative frequency (e.g., 30 Hz) for the following 10 seconds to activate slow-twitch muscle fibers.

In the example of FIG. 3, therapy delivery module 64 drives a single lead 28. Specifically, therapy delivery module 64 delivers electrical stimulation to tissue of patient 14 via selected electrodes 26A-26D carried by lead 28. A proximal end of lead 28 extends from the housing of IMD 20 and a distal end of lead 28 extends to target therapy sites within the pelvic floor, such as tissue sites proximate a sacral nerve, a pudendal nerve, a hypogastric nerve, a urinary sphincter, or any combination thereof. In other examples, therapy delivery module 64 may deliver electrical stimulation with electrodes on more than one lead and each of the leads may carry one or more electrodes. The leads may be configured as an axial leads with ring electrodes and/or paddle leads with electrode pads arranged in a two-dimensional array. The electrodes may operate in a bipolar or multi-polar configuration with other electrodes, or may operate in a unipolar configuration referenced to an electrode carried by the device housing or "can" of IMD 20, e.g., housing 52.

In some examples, processor 56 controls therapy deliver module 64 to generate and deliver the second stimulation therapy to patient 14 based on signals received from acoustic module 66. Acoustic module 66 may include one or more analog circuits, processors, or even software modules. Acoustic module 66 may be configured to control the production of transmitted pressure waves from the portion of housing 52 with actuator circuit 68 and actuator element 72. When controlled by processor 56 to produce and transmit pressure waves, acoustic module 66 controls actuator circuit 68 to produce mechanical pressure waves with actuator element 72, which contacts free wall 54 of housing 52. Actuator element 72 may be permanently coupled to the interior of housing 52 or only contact the housing when needed to produce vibrations in housing 52.

Acoustic module 66 may also be configured to control the detection of pressure waves generated by free wall 54 and actuator element and reflected by tissue and/or bodily fluids within patient 14. In the example shown in FIG. 3, actuator module 66 includes detector element 74 and detector circuit 70, which is configured to detect of the reflected pressure waves. When controlled by processor 56 to detect reflected pressure waves, or in response to producing pressure waves, acoustic module 66 controls detector circuit 70 to detect any pressure waves received by the housing 52. For example, detector element 74 may contact free wall 54 of housing 52 to detect free wall motion caused by impacting reflected pressure waves. Detector circuit 70 may be connected to detector element 74 via an electrical connection and/or a mechanical connection that transmits signals from detector element 74 to detector circuit 70. Detector circuit 70 may thus detect the electrical or mechanical signals generated by detector element 74. Detector circuit 70 may then relay the detection of reflected pressure waves to acoustic module 66.

Acoustic module 66 may communicate the produced and reflected pressure wave information to processor 56. In some examples, processor 56 determines the physiological condition, e.g., bladder fullness state, according to the detection and instructions stored in memory 58 and bladder data 62 and based on the rate detection signals from acoustic module 66. Bladder data 62 may include, for example, one or more thresholds for the bladder fullness state that indicate when stimulation therapy is adjusted by processor 56 to avoid undesired voiding. In some examples, processor 56 generates a notification (also referred to as an alert) that is delivered to patient 14 to avoid a potential leakage event. Processor 56 may also store the determined physiological condition in bladder data 62 and/or use the determined physiological condition to adjust a stimulation parameter or therapy program. In other examples, acoustic module 66 or another processor of IMD 20 may determine the physiological condition based upon the detection of reflected pressure waves and communicate the condition to processor 56 to use and/or storage in bladder data 62.

Actuator element 72 and detector element 74 may be any transducer, material, or device capable of producing and detecting vibrations in the housing 52 corresponding to pressure waves within patient 14. Example transducers may include electroactive polymers, microelectromechanical systems, accelerometers, or piezoelectric crystals. It is also noted that one or both of actuator element 72 and detector element 74 may not need to contact housing 52 to produce and detect pressure waves. For example, a speaker may use air pressure within housing 52 to induce motion of the free wall of the housing to generate pressure waves and a microphone may detect changes in air pressure within IMD 20 caused by reflected pressure waves contacting the free wall of housing 52.

In other examples, actuator element 72 and detector element 74 may be a single element. Actuator element 72 and detector element 74 may be, for example, a single piezoelectric element that transforms energy between mechanical and electrical states. Accordingly, in some examples, actuator circuit 68 and detector circuit 70 may be a single electrical circuit that both produces and detects pressure waves with housing 52 of IMD 20.

In some examples, acoustic module 66 employs a blanking interval between producing transmitted pressure waves and detection of reflected pressure waves. That is, after the transmitted pressure waves are produced, there can be a period of time in which no reflected pressure waves or noise is detected or when the detected pressure waves are not used to determine a physiological condition of patient 14. For example, during the blanking interval, acoustic module 66 may not actively detect any pressure waves contacting the housing of IMD 20. Once the blanking interval has elapsed, acoustic module 66 may actively detect reflected pressure waves or begin detecting pressure waves that are later used to determine a physiological condition of patient 14. The blanking interval may be preset based upon the known distance between IMD 20 and target structures, known intervening structures, medium wave propagation speeds, or other criteria. The blanking interval may be stored by acoustic module 66 or memory 58 and used by processor 56 to control acoustic module 66.

In addition to acoustic module 66, in some examples, IMD 20 may include sensor 76, which processor 56 can use to obtain additional information regarding patient 14. For example, sensor 76 may include a pressure sensor for detecting changes in bladder pressure, electrodes for sensing pudendal or sacral afferent nerve signals, electrodes for sensing external urinary sphincter EMG signals (or anal sphincter signals in examples in which IMD 20 provides fecal incontinence therapy), or any combination thereof. In addition, or instead, sensor 76 may include a motion sensor, such as a two-axis accelerometer, three-axis accelerometer, one or more gyroscopes, pressure transducers, piezoelectric crystals, or other sensors that generate a signal that changes as patient activity level or posture state changes. Processor 56 may be configured to detect a patient condition indicative of a high probability of an incontinence event (e.g., bladder contraction or abnormal detrusor muscle activity) or other events based on signals received from sensor 76 in addition to acoustic module 66. As another example, sensor 76 may also include a motion sensor that is responsive to tapping (e.g., by patient 14) on skin superior to IMD 20 and, as previously described, processor 56 may control therapy delivery module 64 to deliver stimulation therapy, manually abort delivery of stimulation therapy, or inhibit the delivery of stimulation therapy, in response to detection of the patient input via tapping.

In examples in which sensor 76 includes a pressure sensor, processor 56 may be configured to determine a pressure value based on signals received from the pressure sensor and compare the determined pressure value to a threshold value stored as bladder data 62 to determine whether the contractions of bladder 12 are indicative of an imminent incontinence event. In examples in which sensor 76 includes an EMG sensor, processor 56 may be configured to generate an EMG from the received signals generated by sensor 76 (e.g., which may sense the muscle activity with one or more sensor positioned near the target muscle) and compare the EMG to one or more templates stored as bladder data 62 to determine whether the contractions of bladder 12 are indicative of an imminent incontinence event. As another example, processor 56 may compare previously collected EMGs to a current EMG to detect changes over time. The techniques for detecting bladder contractions may also be applied to detecting abnormal detrusor muscle activities. Therefore, sensor 76 may be used to complement the determination of the bladder fullness state based on detected pressure waves generated by acoustic module 66 and reflected by bladder 14. Sensor 76 may be used to confirm a determined physiological condition, e.g., bladder fullness state, indicate when acoustic detection is inappropriate due to a patient activity, or even indicate when acoustic module may require calibration.

Processor 56 may be configured to control therapy delivery module 64 to deliver stimulation therapy based on patient input received via telemetry module 78. Telemetry module 78 includes any suitable hardware, firmware, software or any combination thereof for communicating with another device, such as programmer 24 (FIG. 1). Under the control of processor 56, telemetry module 78 may receive downlink telemetry, e.g., patient input, from and send uplink telemetry, e.g., an alert, to programmer 24 with the aid of an antenna, which may be internal and/or external. Processor 56 may provide the data to be uplinked to programmer 24 and the control signals for the telemetry circuit within telemetry module 78, and receive data from telemetry module 78.

Processor 56 may control telemetry module 78 to exchange information with medical device programmer 24. Processor 56 may transmit operational information and receive stimulation programs or stimulation parameter adjustments via telemetry module 78. Also, in some examples, IMD 20 may communicate with other implanted devices, such as stimulators, control devices, or sensors, via telemetry module 78.

In an example in which telemetry module 78 receives patient input indicating a voluntary voiding event, processor 56 may suspend delivery of stimulation therapy for a pre-determined period of time, e.g., 2 minutes, in response to receiving the patient input. In response to receiving the input, processor 56 may ignore signals indicative of the patient parameter (e.g., processor 56 may not take any action based on the patient parameter), such as determination of changing bladder fullness states or other physiological conditions from acoustic module 66. Processor 56 may ignore these signals for a pre-determined period of time, such as approximately two minutes. After two minutes has elapse, processor 56 may continue monitoring patient 14 to detect the bladder fullness state. Processor 56 may still monitor conditions of patient 14 without taking action, e.g., monitoring a change in bladder fullness state or urine flow out of bladder 12.

The processors described in this disclosure, such as processor 56 and processing circuitry in acoustic module 66 and other modules, may include one or more digital signal processors (DSPs), general purpose microprocessors, application specific integrated circuits (ASICs), field programmable logic arrays (FPGAs), or other equivalent integrated or discreet logic circuitry, or combinations thereof. The functions attributed to processors described herein may be provided by a hardware device and embodied as software, firmware, hardware, or any combination thereof. In some examples, the processing circuitry of acoustic module 66 and/or detector circuit 70 that detects the pressure waves or determines when to produce a pressure wave may be the same microprocessor, ASIC, DSP, or other digital logic circuitry that forms at least part of processor 56.

Memory 58 may also store instructions for execution by processor 56, in addition to stimulation therapy programs 60 and bladder data 62. Information related to pressure wave production and measurement and patient posture may be recorded for long-term storage and retrieval by a user, or used by processor 56 for adjustment of stimulation parameters, such as amplitude, pulse width, and pulse rate. Memory 58 may include one memory or separate memories for storing instructions, electrical signal information, stimulation programs, and bladder data.

Memory 58, as well as other memories described herein, may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. Memory 58 may store program instructions that, when executed by processor 56, cause IMD 20 to perform the functions ascribed to IMD 20 herein.

Power source 80 is configured to deliver operating power to the components of IMD 20. Power source 80 may include a battery and a power generation circuit to produce the operating power. In some examples, the battery may be rechargeable to allow extended operation. Recharging may be accomplished through proximal inductive interaction between an external charger and an inductive charging coil within IMD 20. In other examples, an external inductive power supply may transcutaneously power IMD 20 whenever stimulation therapy is to occur.

Figure 4:
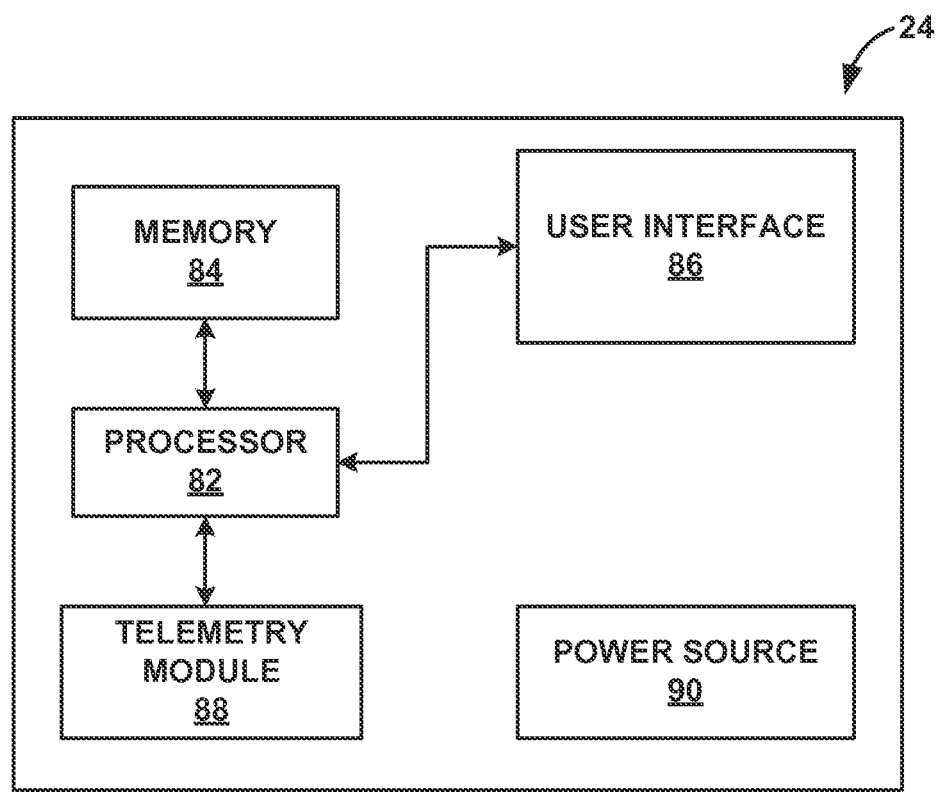
FIG. 4 is a block diagram illustrating an example configuration of the external programmer of the system shown in FIG. 1.

FIG. 4 is a block diagram illustrating example components of external programmer 24. While programmer 24 may generally be described as a hand-held computing device, the programmer may be a notebook computer, a cell phone, or a workstation, for example. As illustrated in FIG. 4, external programmer 24 may include a processor 82, memory 84, user interface 86, telemetry module 88, and power source 90. Memory 84 may store program instructions that, when executed by processor 82, cause processor 82 and external programmer 24 to provide the functionality ascribed to external programmer 24 throughout this disclosure.

In some examples, memory 84 may further include program information, e.g., therapy programs defining the type of stimulation therapy similar to those stored in memory 58 of IMD 20. In other examples, memory 84 may also store two or more therapy programs to be evaluated by patient 14 for efficacy. The stimulation programs stored in memory 84 may be downloaded into memory 58 of IMD 20. Memory 84 may include any volatile, non-volatile, fixed, removable, magnetic, optical, or electrical media, such as RAM, ROM, CD-ROM, hard disk, removable magnetic disk, memory cards or sticks, NVRAM, EEPROM, flash memory, and the like. Processor 82 can take the form one or more microprocessors, DSPs, ASICs, FPGAs, programmable logic circuitry, or the like, and the functions attributed to processor 82 herein may be embodied as hardware, firmware, software or any combination thereof.

User interface 86 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 82 may present and receive information relating to stimulation therapy via user interface 86. For example, processor 82 may receive patient input via user interface 86. The input may be, for example, in the form of pressing a button on a keypad or selecting an icon from a touch screen.

Processor 82 may also be configured to present information to patient 14 or another user via user interface 86, e.g., in the form of alerts related to delivery of the second stimulation therapy to patient 14, detection of a particular bladder fullness state, and the like. Although not shown, external programmer 24 may additionally or alternatively include a data or network interface to another computing device, to facilitate communication with the other device, and presentation of information relating to first and second stimulation therapies or the bladder fullness state of patient 14 detected via IMD 20 via the other device.

Telemetry module 88 supports wireless communication between IMD 20 and external programmer 24 under the control of processor 82. Telemetry module 88 may also be configured to communicate with another computing device via wireless communication techniques, or direct communication through a wired connection. Telemetry module 88 may be substantially similar to telemetry module 78 described above, providing wireless communication via an RF or proximal inductive medium. In some examples, telemetry module 88 may include an antenna, which may take on a variety of forms, such as an internal or external antenna. An external antenna that is coupled to programmer 24 may correspond to a programming head that may be placed over IMD 20.

Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

IMD 20 and/or programmer 24 may control of the timing of the delivery of different types of stimulation therapies that generate different physiological responses to manage urinary or fecal incontinence. If external programmer 24 controls the stimulation, programmer 24 may transmit therapy programs for implementation by IMD 20 to IMD 20 via telemetry module 88. A user (e.g., patient 14 or a clinician) may select the stimulation therapy programs from a list provided via a display of user interface 86. Alternatively, external programmer 24 may transmit a signal to IMD 20 indicating that IMD 20 should execute locally stored programs or therapy routines. In such a manner, control over the electrical stimulation may be distributed between IMD 20 and external programmer 24, or may reside in either one alone.

In one example, patient 14 may control the stimulation therapy delivered by IMD 20 via external programmer 24. For example, patient 14 may initiate or terminate delivery of either the stimulation therapy delivered by IMD 20 via external programmer 24. For example, patient 14 may selectively control the delivery of the stimulation therapy by IMD 20 through input entered via user interface 86. That is, IMD 20 may deliver stimulation therapy based on and in response to patient input entered via user interface 86. In this way, patient 14 may use programmer 24 to deliver the one or more stimulation therapies "on demand," such as when patient 14 senses the onset of a leakage episode or is notified of a particular bladder fullness state (e.g., a relatively full state in which an imminent involuntary voiding event is likely to occur).

In another example, programmer 24 may present a notification indicative of the prospective delivery of a different or additional stimulation therapy to patient 14 via user interface 86. In some examples, this other stimulation therapy may be selected based upon the determined bladder fullness state indicated by acoustic module 66 of IMD 20. As an example, prior to changing stimulation therapy, processor 82 of programmer 24 may generate and present a notification that indicates the new stimulation therapy will be delivered within an indicated period of time. IMD 20 may provide an indication to programmer 24 via the respective telemetry modules 58, 88 that IMD 20 intends on delivering the new stimulation therapy. In some examples, programmer 24 may notify patient 14 by presenting a warning message on a display of user interface 86, emitting an audible alert, or generating a somatosensory alert (e.g., a vibrating housing). In such an example, programmer 24 may prompt patient 14 for input via a display of user interface 86. Patient 14 may enter input via user interface 86 that either confirms delivery of the new stimulation therapy or input for manually aborting the new stimulation therapy. In either case, the patient input is transmitted to IMD 20 via telemetry module 88.

In some examples, patient 14 may also indicate an intent to void via user interface 86, and processor 82 may initiate a stimulation blanking interval (separate from blanking intervals used to detect reflected pressure waves) through communication of the indication to IMD 20 via telemetry module 88. For example, processor 82 may transmit a command signal to IMD 20 that indicates IMD 20 should temporarily suspend delivery of the stimulation therapy. In some cases, this may permit voluntary voiding by patient 14. In some examples, the length of time for a voiding event may be determined by pressing and holding down a button of user interface 86 for the duration of a voiding event, pressing a button a first time to initiate voiding and a second time when voiding is complete, or based on a predetermined period of time following the indication of voluntary voiding provided by patient 14. In each case, programmer 24 causes IMD 20 to temporarily suspend any stimulation therapy so that voluntary voiding is possible.

In other examples, IMD 20 may automatically determine when patient 14 is attempting to voluntarily void, e.g., based on a voiding signature of an EMG signal indicative of bladder activity or based on bladder pressure or contraction. The EMG signal can be generated by, for example, sensor 76 of IMD 20 (FIG. 3) or another sensor that is external to patient 14 or implanted within patient 14. In such examples, IMD 20 may automatically suspend the delivery of stimulation therapy to permit patient 14 to voluntary void. In some cases, suspension of stimulation by IMD 20 is not necessary to facilitate voiding, and stimulation may occur substantially simultaneously with the voluntary voiding. For example, the bladder volume will eventually increase to a level to trigger strong bladder contractions that prevails over the second stimulation therapy to allow voiding.

User interface 86 may also present the current bladder fullness state, or historic bladder fullness states, to a user. For example, user interface 86 may present the bladder fullness state when notifying (or alerting) patient 14 that voiding may be imminent based upon the detected pressure waves from the bladder. In addition, or instead, user interface 86 may present the bladder fullness states over a previous period of time so that the user may review trends in the physiological condition of patient 14. Based on this information, bladder fullness state monitoring and/or stimulation therapy may be adjusted with programmer 24 via user interface 86.

Power source 90 is configured to deliver operating power to the components of programmer 24. Power source 90 may include a battery and a power generation circuit to produce the operating power. In some examples, the battery may be rechargeable to allow extended operation. Recharging may be accomplished by electrically coupling power source 90 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 90 may include circuitry to monitor power remaining within a battery. In this manner, user interface 86 may provide a current battery level indicator or low battery level indicator when the battery needs to be replaced or recharged. In some cases, power source 90 may be capable of estimating the remaining time of operation using the current battery.

Figure 5:
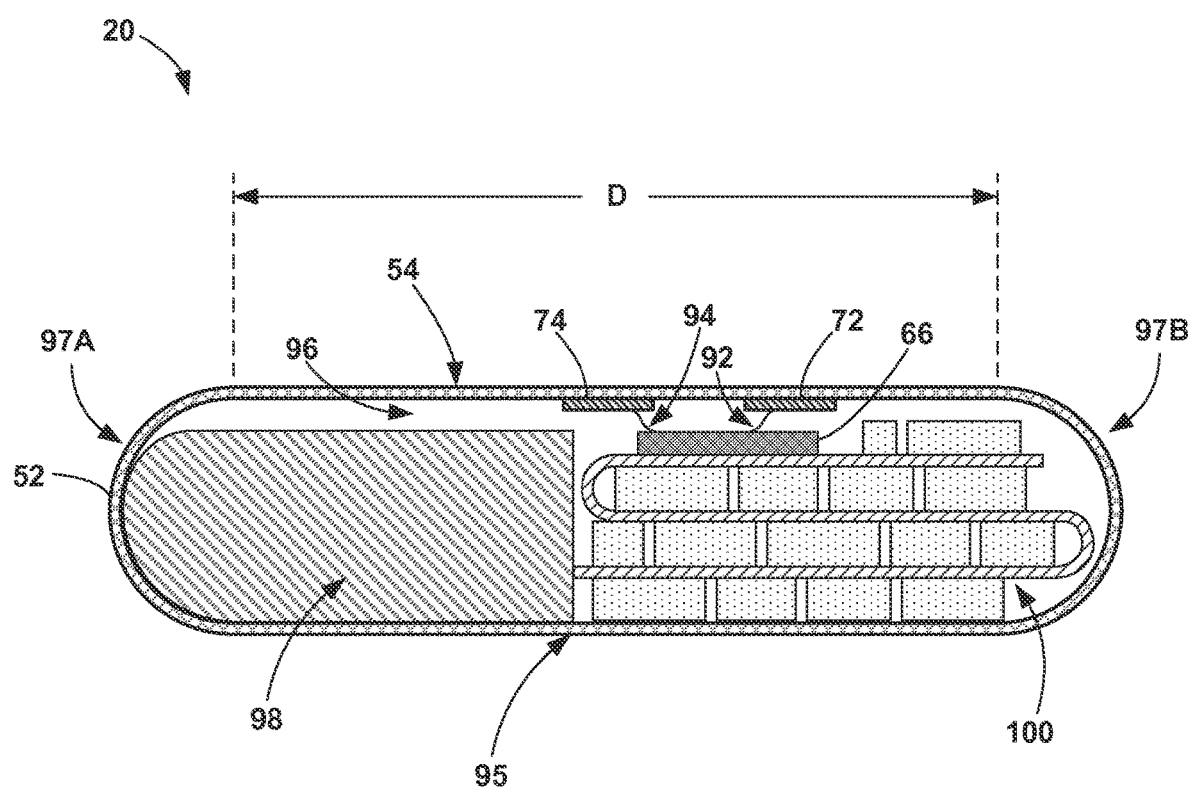
FIG. 5 is a conceptual cross-sectional diagram illustrating an example IMD that uses a portion of the IMD housing to produce and detect pressure waves.

FIG. 5 is a conceptual diagram illustrating an example IMD 20 with free wall 54, which is a portion of housing 52 that is used to produce and detect pressure waves. As shown in FIG. 5, IMD 20 includes outer housing 52, battery 98, operational circuitry 100, acoustic module 66, actuator element 72, detector element 74, and connector ribbons 92 and 94. Because FIG. 5 is a schematic cross-section of IMD 20, not all elements of IMD 20 are shown. In the example shown in FIG. 5, the majority of volume within outer housing 52 is occupied by battery 98 and operational circuitry 100. Battery 98 may be part of power source 80 of FIG. 4 and operational circuitry may include such elements as processor 56, memory 54, therapy delivery module 56, telemetry module 78, and sensor 76 of FIG. 4. Operational circuitry 100 is shown configured as a part of a flexible circuit to fit within housing 52, but operational circuitry 100 may be configured in any form in other examples.

Housing 52 of IMD 20 is a device housing, and the main housing that protects components of IMD 20 from bodily tissues and fluids. Housing 52 substantially encloses (e.g., completely encloses or nearly completely encloses) battery 98, operational circuitry 100, acoustic module 66, actuator element 72, detector element 74, and connector ribbons 92 and 94, and, in some examples, is hermetically sealed. In the example of FIG. 5, housing 52 includes mounting wall 95 that provides a mounting surface for battery 98, operational circuitry 100, or other components. Housing 52 also includes free wall 54. Free wall 54 is a portion of housing 52 that is configured to move (e.g., vibrate or oscillate) relative to other portions of housing 52, as well as relative to battery 98, operational circuitry 100, or other components of IMD 20 in some examples. Few, if any (e.g., sometimes none), rigid components are attached or mounted to free wall 54, thereby permitting free wall 54 freedom of motion to vibrate. Free space 96 is the volume of space within housing 52 adjacent to free wall 54 that allows free wall 54 to move in relation to the rest of housing 52. Free space 96 may be a vacuum or filled with air, filled with a gas mixture, or filled with an inert single gas. Although free space 96 may be of any volume, the distance between the inside surface of free wall 54 and other components is at least large enough to allow free wall 54 to move enough to produce the pressure waves of the desired frequency or to receive the reflected pressure waves. In the example shown in FIG. 5, the curved side walls of housing 52 provide a relatively stiff support structure for free wall 54.

Actuator element 72 and detector element 74 contact free wall 54 either directly or indirectly (e.g., via an intervening adhesive or other intervening component). Acoustic module 66 is electrically coupled to actuator element 72 via conductive ribbon 92 and detector element 74 via conductive ribbon 94 passing through free space 96. As discussed with regard to FIG. 3, actuator element 72 is configured to produce pressure waves by causing motion of free wall 54 (e.g., oscillations of free wall 54). The produced pressure waves are transmitted away from free wall 54 and IMD 20. At least some of the transmitted pressure waves that reflect off of anatomical structures or other changes in medium density traverse back through patient 14 to contact free wall 54. The contact made by the reflected pressure waves causes vibration or motion in free wall 54. Detector element 74 contacting free wall 54 is configured to detect these vibrations or motions and converts them to electrical signals with which acoustic module 66 may determine a bladder fullness state of patient 14. The degree of free wall 54 motion (also referred to herein as deflection) may depend upon the frequency of the pressure waves produced and received by free wall 54. As further discussed in FIG. 3, other examples may include different variations of actuator element 72 and detector element 74, such as a single transducer element.

Free wall 54 may be constructed of a similar thickness as mounting wall 95 and the rest of housing 52. In other examples, free wall 54 may be constructed with a smaller or larger thickness to tune free wall 54 to the frequency of pressure waves required to determine the desired physiological condition. In some examples, the thickness of free wall 54 may be between approximately 0.1 millimeters (mm) and 5 mm. However, free wall 54 may be constructed with any thickness in other examples, which can be selected to generate the desired pressure wave frequency. The other dimensions of free wall 54 may also vary depending upon the type of pressure waves desired.

In some examples, free wall 54 may generally be circular in shape, although in other examples, any other polygons or irregular shapes may be used. Distance D represents the diameter of free wall 54 in the example shown in FIG. 5. In some examples, distance D may generally be the length of the substantially flat (planar) portion of housing 52, up to the curved side walls 97A and 97B. In some examples, distance D is between approximately 2.0 mm and 70 mm. However, free wall 54 may be constructed with any width and surface area.

As shown in FIG. 5, free wall 54 is substantially planar. However, in other examples, free wall 54 may be constructed in various convex configurations, concave configurations or other curvilinear or nonplanar configurations. Different configurations may focus the transmission of pressure waves to desired anatomical structures or collect reflected pressure waves from multiple locations. In addition, free wall 54 may be constructed with varying thicknesses across the free wall to appropriately tune free wall 54 to the desired pressure wave transmission and detection frequencies. As discussed herein, in some examples, housing 52 may be configured with multiple free walls that are each capable of producing and/or detecting pressure waves.

Housing 52 may be constructed of a single material in some examples. Example materials may include biocompatible materials such as metal alloys (e.g., stainless steel or titanium alloys) pure metals, composites, or polymers. Alternatively, housing 52 may be constructed of various materials. For example, housing 52 may be generally constructed of a titanium alloy while free wall 54 may be constructed of a ceramic composite. Housing 52 may be constructed of any combination of materials. In addition, housing 52 may be constructed in any variety of shapes and sizes configured to implant IMD 20 at specific locations within patient 14.

In other examples, a material may be added to the external surface of free wall 54 to help transmit pressure waves between free wall 54 and the tissues of patient 14. For example, a biocompatible gel or polymer that maintains contact with tissue until the healing process has completed after implantation may be positioned on an outer surface of free wall 54 that contacts tissue of patient 14 when IMD 20 is implanted in patient 14. For example, the material may be configured to degrade over time to allow a sufficient tissue-housing interface to develop. In other examples, the material may be designed to minimize dense scar tissue from developing against free wall 54 that may dampen the transmission of pressure waves between free wall 54 and adjacent patient tissue (e.g., an anti-inflammatory agent steroid, or a biocompatible material).

Figure 6:
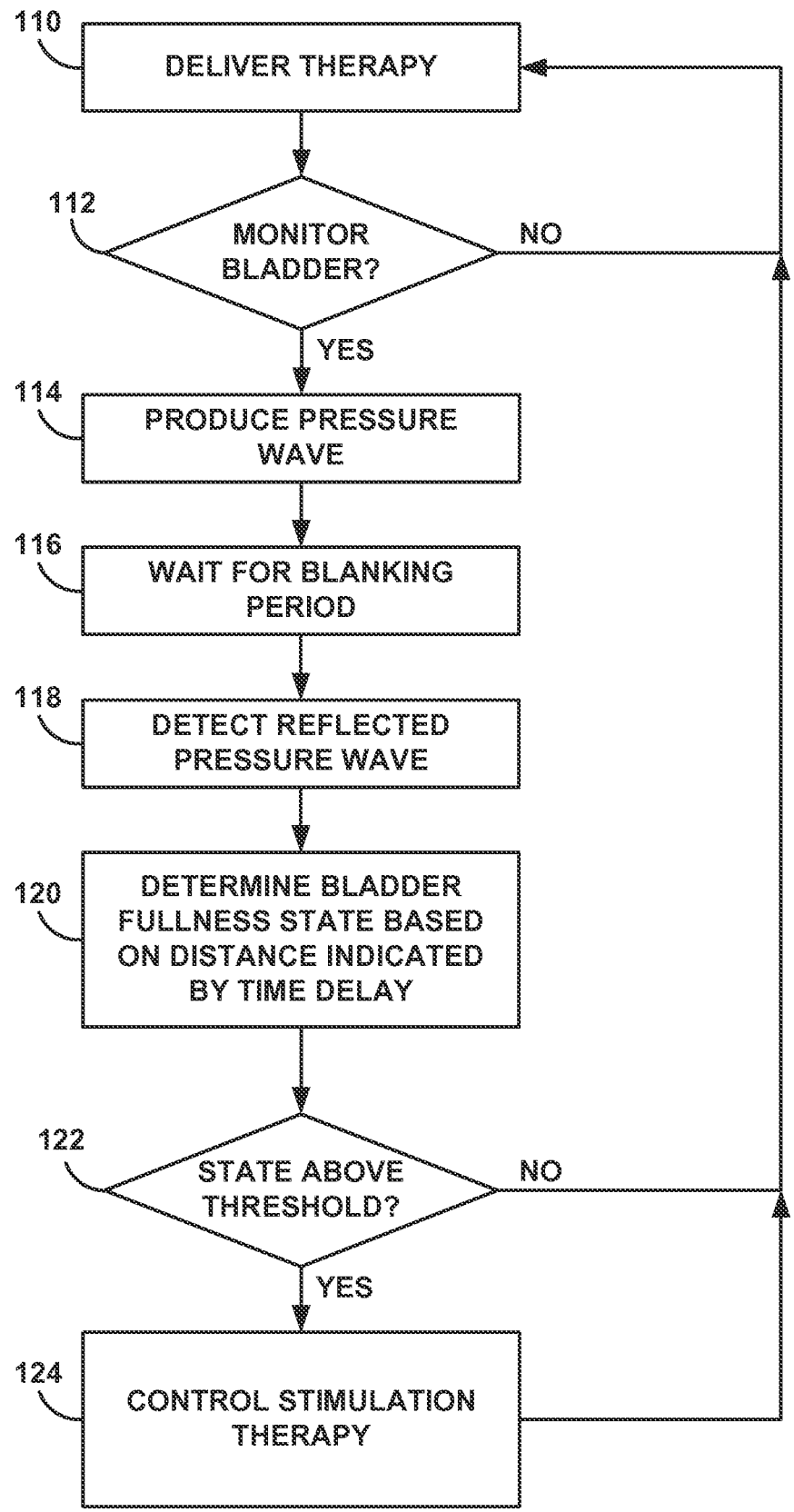
FIGS. 6 and 7 are flow diagrams illustrating example techniques for determining a physiological condition of a patient using pressure waves detected by an IMD housing.

FIG. 6 is a flow diagram illustrating an example technique for determining a bladder fullness state with pressure waves generated and detected by the housing of IMD 20. As shown in FIG. 6, IMD 20 delivers stimulation therapy according to one or more therapy programs (110). In response to determining that it is not time to monitor the bladder fullness state, e.g., based upon a timer or patient 14 condition ("NO" branch of block 112), processor 56 of IMD 20 continues to deliver therapy (110). A condition of patient 14 that may prevent monitoring the bladder fullness state may include, for example, voiding or activity detected that would interfere with accurate detection of the bladder fullness state. In response to determining that the bladder fullness state should be monitored ("YES" branch of block 112), processor 56 controls acoustic module 66 to produce and transmit pressure waves (114).

Acoustic module 66 controls actuator 72 to produce a pressure wave with free wall 54 of housing 52, where the pressure wave is transmitted away from IMD 20 (114). In the example shown in FIG. 6, acoustic module 66 waits for a duration of time, which can be referred to as a blanking period, before detecting any reflected pressure waves (116). As described herein, the reflected pressure waves originate from anatomical structures or other tissues contacted by the produced pressure wave transmitted away from IMD 20. After the blanking period, acoustic module 66 controls detector 74 to detect reflected pressure waves from the proximal wall of bladder 12 received by free wall 54 of housing 52 (118). Free wall 54 moves in response to pressure waves incident on free wall 54, and detector 74 may detect movement of free wall 54 and generates a signal that is modulated based on the movement of free wall 54.

Acoustic module 66 converts the detection signal from detector 74 to a signal representative of the detection of pressure waves and communicates the signal to processor 56. Processor 56 determines a bladder fullness state based upon the distance indicated by the time delay between the time at which actuator 72 and free wall 54 generated and transmitted the pressure wave into patient 14 and the time at which detector 74 detected the reflected pressure wave (120). A decrease in the time delay may indicate that the distance between free wall 54 and the proximate wall of bladder 12, which the pressure wave reflected off, has decreased. This decrease in distance between free wall 54 and the proximate wall of bladder 12 may correlate to a increase in the volume of bladder 12. In some examples, acoustic module 66 may produce and detect multiple pressure waves and processor 56 to determine the bladder fullness state based on multiple detected pressure waves, e.g., ultrasound imaging techniques.

In response to determining the determined bladder fullness state is below a fullness threshold ("NO" branch of block 122), processor 56 continues to control therapy delivery module 64 (FIG. 3) to deliver therapy (110). The threshold for the bladder fullness state may be defined as a time delay for the reflected pressure waves or a determined size of bladder 12, depending upon the values used by processor 56. In response to determining the determined bladder fullness state is above the fullness threshold ("YES" branch of block 122), processor 56 controls therapy delivery module 64 to deliver stimulation therapy to patient 14, where the electrical stimulation is configured to compensate for the determined bladder fullness state (124), e.g., to help prevent an incontinence event. Stimulation control may be in the form of adjusting a single stimulation parameter, e.g., increasing a voltage amplitude value or frequency (e.g., according to therapy adjustment instructions associated with the detected bladder fullness state in memory 58), or delivering stimulation according to a different or additional therapy program (e.g., a stimulation therapy program 60 associated with the detected bladder fullness state in memory 58), or delivering a second stimulation therapy, e.g., a "boost" to the first stimulation therapy already delivered to patient 14. Processor 56 then continues to control therapy delivery module 64 (FIG. 3) to deliver therapy to patient 14 according to the adjusted stimulation therapy (110).

In other examples, processor 56 may adjust stimulation at times other than when the bladder fullness state is at or above the fullness threshold. For example, the bladder fullness state may be compared to a stepped threshold table or algorithm in which multiple therapy adjustments are made based upon the changing bladder fullness state. For example, processor 56 may incrementally change a stimulation parameter value or load different therapy programs based upon the most recent bladder fullness state determination. These thresholds or algorithms may be selected or generated by a user for more customized stimulation therapy.

In other examples, processor 56 may control acoustic module 66 to produce more than one pressure wave in block 114. Processor 56 may instead control acoustic module 66 to produce a set of pressure waves or a wave train of multiple pressure waves. These pressure waves may be produced at a single predetermined frequency (e.g., known to processor 56 prior to the generation of the pressure waves). Upon detecting reflected pressure waves with detector 74, acoustic module 66 or processor 56 may filter the detected pressures for the frequency or frequency band of pressure waves produced by acoustic module 66, or the frequency of pressure waves anticipated by acoustic module 66. In this manner, acoustic module 66 may identify reflected pressure waves from noise or other waves traveling through patient 14.

Figure 7:
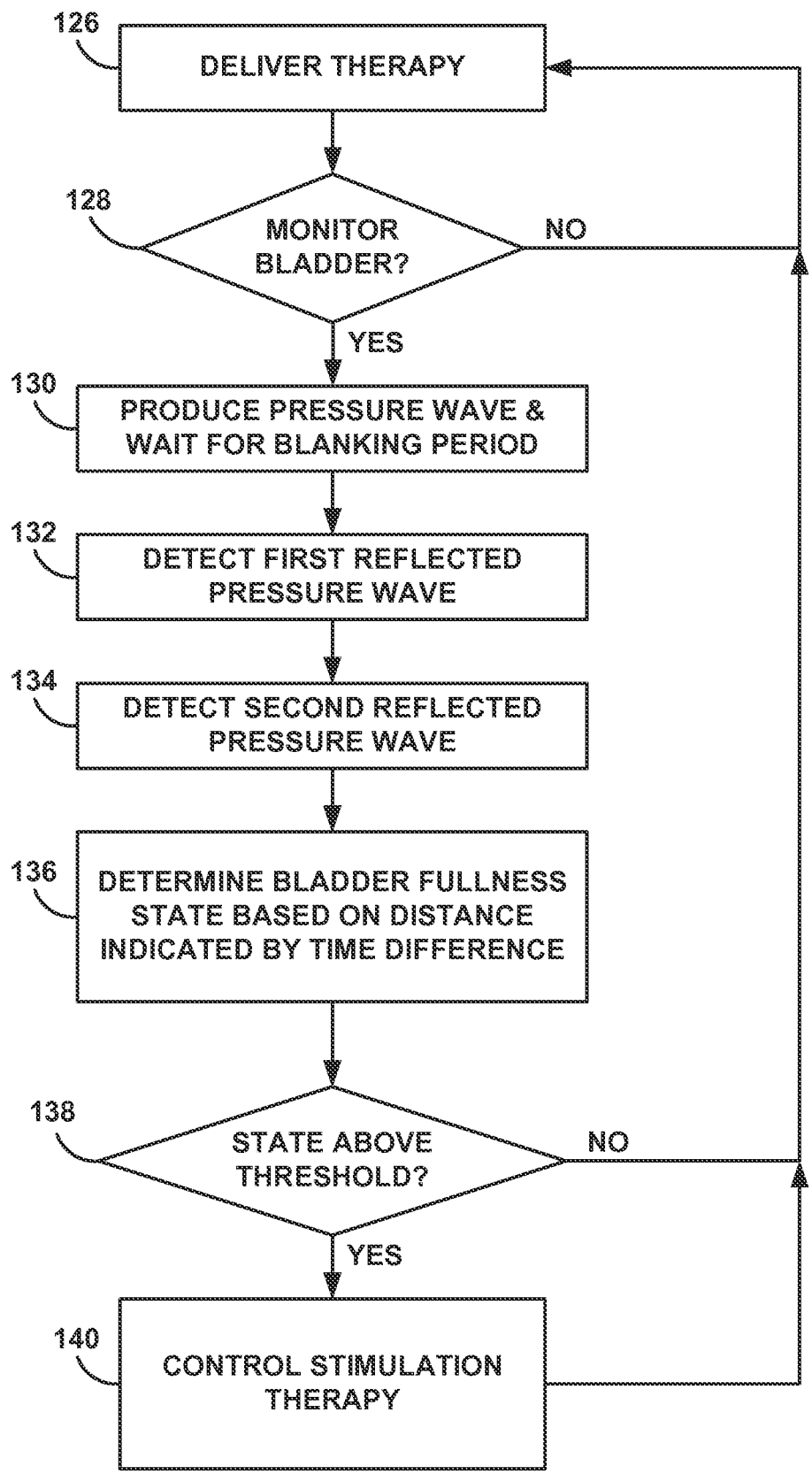

FIG. 7 is flow diagram illustrating an example technique for determining a physiological condition of a patient based on pressure waves that indicate a distance between opposing walls of bladder 12. FIG. 7 is similar to FIG. 6, but processor 56 determines the bladder fullness state using opposing walls of bladder 12; the distance between the opposing walls of bladder 12 can indicate a current bladder volume. As shown in FIG. 7, IMD 20 delivers stimulation therapy according to one or more therapy programs (126). In response to determining that it is not time to monitor the bladder fullness state, e.g., based upon a timer or patient 14 condition ("NO" branch of block 128), processor 56 continues to control therapy delivery module 64 to deliver therapy to patient 14 (126). In response to the bladder fullness state should be monitored ("YES" branch of block 128), processor 56 controls acoustic module 66 to produce and transmit pressure waves (130).

Acoustic module 66 controls actuator 72 to produce a pressure wave with free wall 54 of housing 52, where the pressure wave is transmitted away from IMD 20, and acoustic module 66 waits for the predetermined blanking period before detecting any reflected pressure waves (130). After the blanking period, acoustic module 66 controls detector 74 to detect a first reflected pressure wave, which likely reflected off of the proximal wall of bladder 12 (132). For example, acoustic module 66 may control detector 74 to detect movement of free wall 54 of housing 52, which may move in response to pressure waves incident on free wall 54. Detector 74 also detects a second reflected pressure wave, which likely reflected off of the distal wall of bladder 12 (134). The second reflected pressure wave may be detected after a predetermined blanking period or other predetermined delay to ignore extraneous reflected pressure waves and capture the reflected pressure waves from the expected location of the distal wall of bladder 12. For example, after detecting the first reflected pressure wave, acoustic module 66 may control detector 74 to detect movement of free wall 54, which may move in response to pressure waves incident on free wall 54. Detector 74 generates a signal that is modulated by movement of free wall 54.

Acoustic module 66 converts the detection signals from detector 74 to signals representative of the detections and communicates the signals to processor 56. Processor 56 can then determine a bladder fullness state based upon the distance indicated by the difference in time delay between the detected first reflected pressure wave and second reflected pressure wave (136). For example, a larger time delay between the first and second reflected pressure waves may indicate a full bladder fullness state. Conversely, a small time delay between the first and second reflected pressure waves may indicate a relatively empty bladder fullness state. The time delays that indicate the full bladder fullness state, empty bladder fullness state, and, in some example, bladder fullness states between the full and empty states, can be predetermined and stored as bladder data 62 (FIG. 3) by IMD 20 or stored by a memory of another device (e.g., programmer 24). In some examples, this acoustic module 66 may produce and detect multiple pressure waves in order for processor 56 to determine the bladder fullness state from opposing walls of bladder 12, e.g., ultrasound imaging techniques.

In response to determining the determined bladder fullness state is below a fullness threshold ("NO" branch of block 138), processor 56 continues to control therapy delivery module 64 to deliver therapy to patient 14 (126). In response to determining the determined bladder fullness state is above the fullness threshold ("YES" branch of block 1138), then processor 56 controls stimulation therapy accordingly to compensate for the determined bladder fullness state (140). Stimulation control may be in the form of initiating delivery of therapy, adjusting a single stimulation parameter, e.g., increasing a voltage amplitude value, or delivering stimulation according to a different or additional therapy program. Processor 56 then continues to deliver therapy according to the adjustment (126).

In some cases, determination of a relative distance between proximate and distal bladder walls may allow for greater specificity in the determination of the bladder fullness state, compared to the determination of bladder state based on a distance between free wall 54 and a single wall of bladder 14, as described with respect to FIG. 6. Although FIGS. 6 and 7 describe IMD 20 as delivering therapy, other examples of IMD 20 may include determining a bladder fullness state, or other physiological condition, without delivering therapy with IMD 20.

In some examples of the techniques of FIGS. 6 and 7, processor 56 may periodically determine the bladder fullness state of patient 14. In some cases, processor 56 determines when to monitor, or update, the bladder fullness state based upon an update timer. When the update timer expires and in response to detecting the expiration of the timer, processor 56 controls acoustic module 66 to use produced and detected pressure waves to determine a current bladder fullness state. The update timer may generally be set to a duration between approximately 1 minute and 60 minutes. An example update timer may be set to 10 minute intervals. In other examples, the update timer may be substantially shorter such that the bladder fullness state is continuously updated. In another example, the update timer may vary based on the activity of patient 14 as detected by sensor 76 or even completely overruled based upon the activity or therapy of patient 14.

In other examples of FIG. 6 or 7, processor 56 may generate a notification for patient 14 or a clinician based on the bladder fullness state instead of or in addition to automatically adjusting stimulation therapy. The notification can be transmitted to patient 14 using any suitable technique, such as by causing housing 52 to vibrate, or by transmitting a signal to programmer 24, which may then generate a visual, audio, and/or somatosensory alert to patient via user interface 86. For example, upon the detection of a bladder fullness state associated with a relatively full bladder (in which a leakage event may be likely to occur), processor 56 may generate a notification that instructs patient 14 to initiate a "boost" of stimulation therapy with programmer 24 to prevent leakage. In addition or instead, processor 54 may generate the notification that causes patient 14 to void bladder 12 and avoid an incontinence event. The notification generated by processor 56 may be transmitted to programmer 24 via telemetry module 78, for example. In some examples, processor 56 can generate a general notification, and patient 14 (or a patient caretaker) may determine which course of action is best (e.g., delivering a boost of stimulation or voluntary voiding) suited for patient 14.

Although FIGS. 6 and 7 are described as being performed by different components of IMD 20, such as acoustic module 66 and processor 56, in other examples, the technique shown in FIGS. 6 and 7 can be controlled by one component or any combination of components, such as processor 82 of programmer 24.

Figure 8:
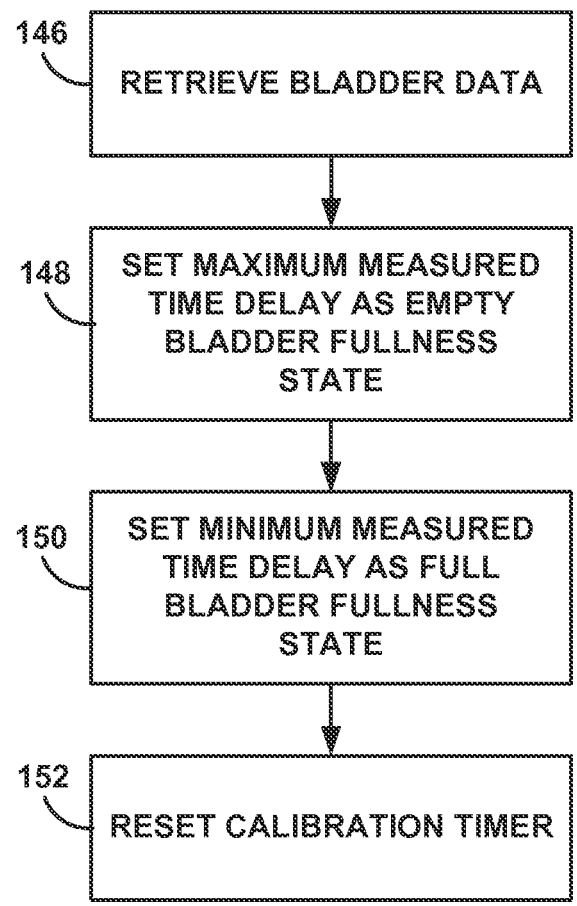
FIGS. 8 and 9 are flow diagrams illustrating example techniques for calibrating an acoustic module to physiological conditions of a patient.

FIG. 8 is a flow diagram illustrating an example technique for calibrating acoustic module 66 to specific bladder fullness states. As shown in FIG. 8, processor 56 of IMD 20 retrieves stored bladder data 62 (FIG. 3), e.g., time delays in reflected pressure waves or determined bladder distances, from memory 58 of IMD 16 or a memory of another device (e.g., programmer 24) (146). In some examples, bladder data 62 stores bladder data for a specific time period, such as the past 24 hours. In other examples, the time period that includes the stored bladder data may be shorter or longer than 24 hours. However, the time period may be selected to include a robust set of data that covers both an empty bladder fullness state and a full bladder fullness state. For calibration purposes, processor 56 can retrieve a subset of the stored data (e.g., the bladder data for the past 12 hours) or all of the stored bladder data.

Processor 56 analyzes the stored bladder data and sets the maximum measured time delay as the empty bladder fullness state (148). Processor 56 then sets the minimum measured time delay as the full bladder fullness state (150). In some examples where IMD 20 utilizes more than an empty and full bladder state, processor 56 may generate other bladder fullness states between the empty and full bladder states. Processor 56 may utilize a linear interpolation technique or more complex equations to model the diameter of bladder 12 and correlate this distance to specific bladder fullness states. This calibration is applicable to bladder fullness states determined with detection of only the proximal wall of bladder 12. However, data indicating a distance between opposing walls of bladder 12 may also be used. In this case, the minimum distance would be set to the empty bladder fullness state and the maximum distance would be set to the full bladder fullness state.

After the calibration, processor 56 resets the calibration timer (152) before controlling therapy delivery module 64 to continuing to deliver therapy and monitor the bladder fullness state (142). The calibration timer may be used to determine when the acoustic module 66 should be calibrated to the bladder fullness states. The calibration timer may be generally set to a time period of hours, weeks, months, or even years. For example, the calibration timer may be set to seven days. A user may adjust the calibration timer. In addition, or instead, processor 56 may initiate calibration upon determination of bladder fullness states that do not follow a logical progression.

Although FIG. 8 is directed to calibration of acoustic module 66 to specific bladder fullness states during therapy, the technique may be used outside of delivering stimulation therapy. For example, the technique of FIG. 8 may be used initially after implantation and before any stimulation therapy is delivered by IMD 20. In addition, or instead, the calibration method may be used during bladder monitoring without any stimulation therapy being delivered.

Figure 9:
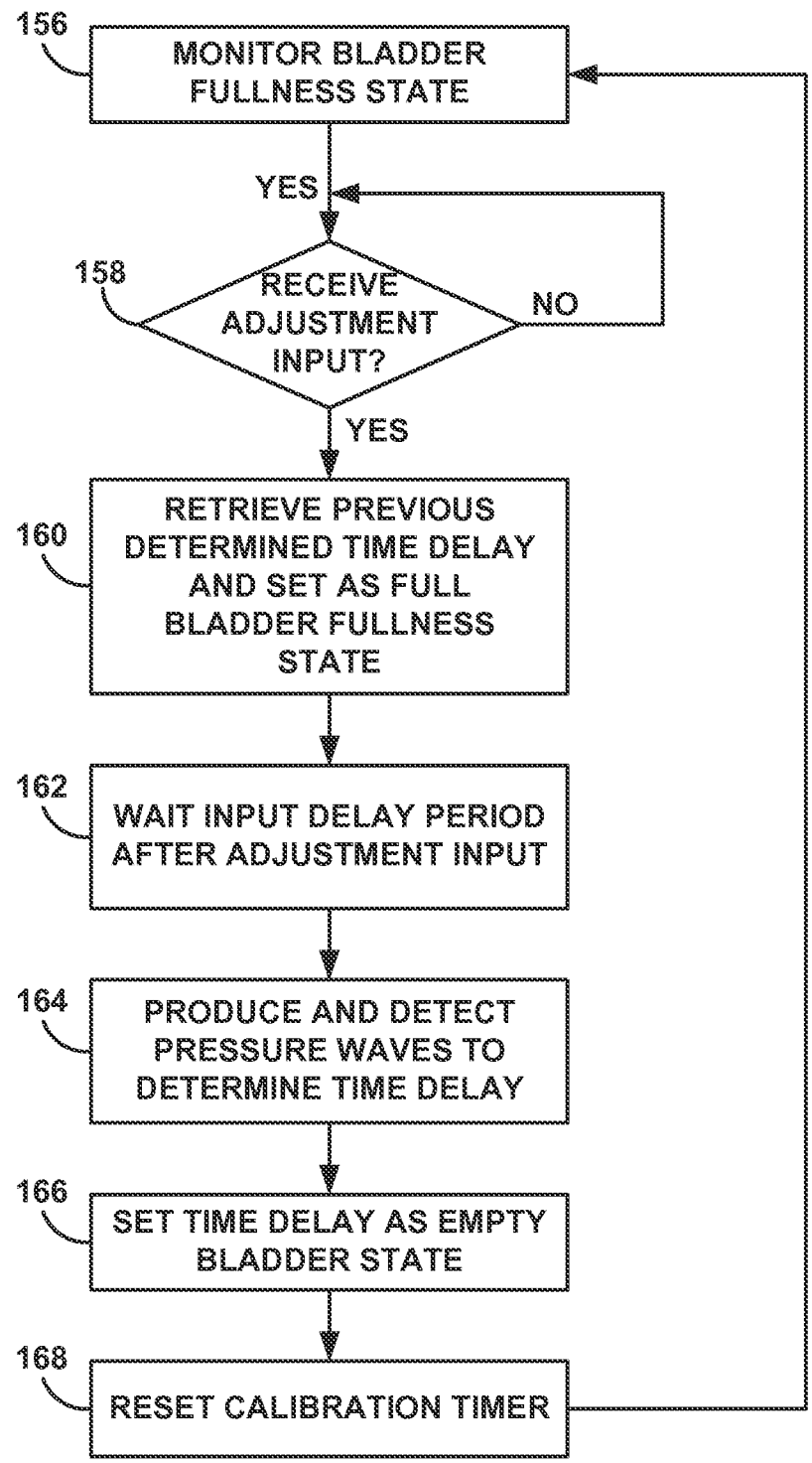

FIG. 9 is a flow diagram illustrating an example technique for calibrating acoustic module 66 to specific bladder fullness states in response to a patient input. Processor 56 of IMD 20 may monitor the bladder fullness state with acoustic module 66 (156). Processor 56 then waits to calibrate acoustic module 66 until user interface 86 of programmer 24 receives a user input for therapy (158). The user input may be a request for additional stimulation therapy, e.g., a "boost," which patient 14 may request for various reasons. These reasons may include, for example, a sensation of imminent voiding or the undertaking of an activity that may increase the likelihood of a stress incontinence event (e.g., exercising, coughing, etc.). The user input may indicate that bladder 12 is full of urine or at least patient 14 perceives the need to void. Once user interface 86 receives the user input from patient 14 ("Yes" branch of block 158), processor 56 continues with calibration. Processor 56 retrieves the previous stored time delay from memory 58, e.g., the most recent determined time delay from reflected pressure waves indicative of the most recently determined bladder fullness state, and associates the time delay with the full bladder fullness state (160). This full bladder fullness state is selected because patient 14 has indicated that voiding is imminent with the therapy adjustment input.

Processor 56 next waits during the input delay period after the adjustment input before continuing (162). Because the bladder fullness state calibration includes a detection of an empty bladder 12, the input delay period is set to allow time for patient 14 to void bladder 12 and achieve the empty bladder state used in the calibration. Generally, the input delay period may be set between approximately 1 minute and 60 minutes. For example, the input delay period may be set to 3 minutes. The input delay period may be immediately following receipt of the adjustment input and set by the user to a time period greater than required for patient 14 to void bladder 12. In other examples, processor 56 may wait for an input confirming that voluntary voiding occurred. After the input delay period expires, processor 56 controls acoustic module 66 to produce transmitted pressure waves and detect the reflected pressure waves with free wall 54 of IMD 20 to determine the time delay between IMD 20 and bladder 12 (164). Processor 56 then sets this time delay as the empty bladder fullness state because patient 14 just emptied bladder 12 (166).

After the calibration, processor 56 may reset the calibration timer (168) before continuing to deliver therapy and monitor the bladder fullness state (154). Similar to FIG. 8, the calibration timer of FIG. 9 may be used to determine when the acoustic module 66 should be calibrated to the bladder fullness states. The calibration timer may be generally set to a time period of hours, weeks, months, or even years. For example, the calibration timer may be set to seven days. In other examples, the user input may simply indicate that patient 14 has voided and bladder 12 is empty. This input may be provided directly by patient 14 using programmer 24.

Although both FIGS. 8 and 9 describe techniques for calibrating the bladder fullness state, each technique may be used to calibrate other physiological conditions to the detected pressure waves from acoustic module 66. Furthermore, although the techniques shown in FIGS. 8 and 9 are described as being performed by processor 56 of IMD 20, in other examples, another processor can perform any part of the technique shown in FIGS. 8 and 9, such as processor 82 of programmer 24 (FIG. 4).

The techniques described in this disclosure may help reduce or eliminate leaking episodes caused by urinary disorders. That is, by determining bladder fullness states to monitor the patient condition, therapy may be selected according to the volume of urine within bladder 12. For example, stimulation therapy may be adjusted with a change to a stimulation parameter or delivery according to a different therapy program based upon the bladder fullness state. In other examples, one or more stimulation therapy programs may be associated with different bladder fullness states. Therefore, stimulation therapy may change as each subsequent bladder fullness state is detected. This type of therapy progression may treat incontinence while also reducing paresthesia and increasing battery life of IMD 20.

In addition, the determination of a bladder fullness state or other physiological conditions with pressure waves produced and detected by a portion housing 52 may be completed without an additional implantable device. Because housing 52 of IMD 20 is configured to be implanted within the patient, no additional sensor needs to be tethered to the IMD housing via a lead or in communication with the processor of the IMD. This small and streamlined package may allow for an objective determination of a physiological condition while reducing implant procedure time, device cost, tissue tunneling, invasiveness, and even system complexity.

Although a bladder fullness state is described herein, any physiological condition may be determined with an acoustic module and detected pressure waves with the IMD housing. Alternative physiological conditions may include colon fullness states, fecal movement, urine flow, stomach volume, gastrointestinal movement, for example.

As described herein, the disclosure includes different techniques, devices, and systems. In one example, a method may include producing a pressure wave within a patient with a portion of a housing of an implantable medical device, wherein the housing substantially encloses a processor, detecting at least one reflected pressure wave with the housing portion, and automatically determining a physiological condition of the patient based on the at least one reflected pressure wave. The housing portion may be part of a device housing configured to enclose operational circuitry of the implantable medical device and the housing portion is tuned to one or more frequencies of the produced pressure wave.

In some examples, producing the pressure wave may include producing the pressure wave from an internal location inferior to a bladder and lateral to a labia and directing the pressure wave towards the bladder. The physiological condition may include a bladder fullness state. In addition, in some examples, determining the physiological condition may include measuring a time delay between the produced pressure wave and the at least one reflected pressure wave and determining a distance between the portion of the implantable medical device housing and an anatomical structure of the patient at which the at least one reflected pressure wave originated based on the time delay.

In some examples, the at least one reflected pressure wave may include a first reflected pressure wave and a second reflected pressure wave, and determining the physiological condition may further include determining a first time delay between the produced pressure wave and the first reflected pressure wave, determining a second time delay between the produced pressure wave and the second reflected pressure wave, and determining a distance between first and second anatomical structures of the patient at which the first and second reflected pressure waves, respectively, originated based on a difference between the first time delay and the second time delay.

In some examples, the method may also include receiving a therapy adjustment input from the patient, determining the physiological condition after an input delay period to set a first state of the physiological condition, retrieving from a memory a last physiological condition determination before the therapy adjustment input was received, and setting a second state of the physiological condition as the last physiological condition determination. In some examples, the method may include delivering electrical stimulation therapy with a therapy delivery module disposed within the implantable medical device and coupled to at least one medical lead and controlling electrical stimulation therapy based on the physiological condition. In addition, in some examples, the method may include generating a patient notification based on the physiological condition. In some examples, producing the pressure wave may include oscillating the portion of a housing of an implantable medical device.

In another example, a system may include an implantable medical device comprising a device housing, an acoustic module configured to produce a pressure wave within a patient with a portion of the device housing and detect at least one reflected pressure wave with the housing portion, and a processor configured to automatically determine a physiological condition of the patient based on the at least one reflected pressure wave, wherein the device housing substantially encloses the processor. The device housing may be configured to enclose operational circuitry of the implantable medical device, and is tuned to one or more frequencies of the pressure wave.

The implantable medical device may be configured to be implanted at an internal location inferior to a bladder and lateral to a labia. The physiological condition may include a bladder fullness state. The acoustic module may be configured to determine a time delay between the produced pressure wave and the at least one reflected pressure wave, and determine a distance between the housing portion and an anatomical structure of the patient at which the at least one reflected pressure wave originated based on the time delay. The at least one reflected pressure wave may include a first reflected pressure wave and a second reflected pressure wave, and the acoustic module may be configured to determine a first time delay between the produced pressure wave and the first reflected pressure wave and determine a second time delay between the produced pressure wave and the second reflected pressure wave, and determine a distance between first and second anatomical structures of the patient at which the first and second reflected pressure waves, respectively, originated based on a difference between the first time delay and the second time delay.

In some examples, the system may include an external programmer that includes a user interface that receives a therapy adjustment input from the patient, wherein the processor determines the physiological condition with the acoustic module after an input delay period to set a first state of the physiological condition, retrieves from a memory a last physiological condition determination before the therapy adjustment input was received, and sets a second state of the physiological condition as the last physiological condition determination.

In other examples, the system may include at least one medical lead coupled to the implantable medical device and a therapy delivery module disposed within the device housing and configured to deliver electrical stimulation therapy to the patient via the at least one medical lead, wherein the processor is configured to control electrical stimulation therapy based on the physiological condition. The system may also include an external programmer configured to present a notification to the patient based on the physiological condition. The acoustic module may be configured to produce the pressure wave with the portion of the device housing by at least causing the portion of the housing to oscillate.

In another example, a system may include means for producing a pressure wave within a patient with a portion of a housing of an implantable medical device, wherein the housing substantially encloses a processor. The system may further include means for detecting at least one reflected pressure wave with the housing portion, and means for automatically determining a physiological condition of the patient based on the at least one reflected pressure wave. In some examples, the housing may be configured to enclose operational circuitry of the implantable medical device, and the housing portion may be tuned to a frequency of the at least one reflected pressure wave. In addition, in some examples, the means for producing a pressure wave may be configured to be implanted at an internal location inferior to a bladder and lateral to a labia. In some examples, the system may further include means for delivering electrical stimulation therapy from a therapy delivery module disposed within the implantable medical device and coupled to at least one medical lead, and means for controlling electrical stimulation therapy based upon the physiological condition.

The techniques described in this disclosure may be implemented in hardware, software, firmware, or any combination thereof. In particular, the techniques may be implemented in a hardware device, such as a wireless communication device or network device, either of which may include software and/or firmware to support the implementation. For portions implemented in software, the techniques may be realized in part by a computer-readable medium comprising program code containing instructions that, when executed, performs one or more of the methods described above. In this case, the computer readable medium may comprise RAM (e.g., synchronous dynamic random access memory (SDRAM)), ROM, NVRAM, EEPROM, FLASH memory, magnetic or optical data storage media, and the like.

The program code may be executed by one or more processors, such as one or more DSPs, general purpose microprocessors, ASICs, FPGAs, or other equivalent integrated or discrete logic circuitry. In this sense, the techniques are implemented in hardware, whether implemented entirely in hardware or in hardware such as a processor executing computer-readable code. Accordingly, the term "processor," as used herein may refer to any of the foregoing structure or any other structure suitable for implementation of the techniques described herein.

Many examples of the disclosure have been described. These and other examples are within the scope of the following claims. Various modifications may be made without departing from the scope of the claims.

What is claimed is:
1. A method comprising:
producing a pressure wave within a patient with a portion of a device housing of an implantable medical device using an actuator element configured to contact the portion of the device housing, wherein the device housing encloses a processor and the actuator element, and wherein the implantable medical device is configured to couple to an implantable medical lead;
detecting at least one reflected pressure wave with the portion of the device housing; and determining, by the processor and based on the at least one reflected pressure wave, a physiological condition of the patient.

2. The method of claim 1, wherein the portion of the device housing is configured to enclose operational circuitry of the implantable medical device, the operational circuitry comprising the processor, and wherein the portion of the device housing is tuned to one or more frequencies at least one of the produced pressure wave or the at least one reflected pressure wave.

3. The method of claim 1, wherein producing the pressure wave further comprises:
producing the pressure wave from an internal location inferior to a bladder and lateral to a labia; and
directing the pressure wave towards the bladder.

4. The method of claim 1, wherein the physiological condition includes a bladder fullness state.

5. The method of claim 1, wherein determining the physiological condition further comprises:
determining a time delay between the produced pressure wave and the at least one reflected pressure wave; and
determining, based on the time delay, a distance between the portion of the device housing and an anatomical structure of the patient from which the at least one reflected pressure wave originated.

6. The method of claim 1, wherein the at least one reflected pressure wave comprises a first reflected pressure wave and a second reflected pressure wave, and wherein determining the physiological condition further comprises:
determining a first time delay between the produced pressure wave and the first reflected pressure wave;
determining a second time delay between the produced pressure wave and the second reflected pressure wave; and
determining a distance between first and second anatomical structures of the patient from which the first and second reflected pressure waves, respectively, originated based on a difference between the first time delay and the second time delay.

7. The method of claim 1, further comprising:
receiving an indication of a therapy adjustment input from the patient, the therapy adjustment input being received by one of the implantable medical device or an external programmer;
determining the physiological condition after an input delay period immediately following receipt of the therapy adjustment input to set the determined physiological condition as a first physiological state of the patient;
retrieving, from a memory, a last physiological condition determination before the therapy adjustment input was received; and
setting the last physiological condition as a second physiological state of the patient.

8. The method of claim 7, further comprising receiving, via a user interface of the external programmer, the therapy adjustment input from the patient, wherein receiving the indication of the therapy adjustment input comprises receiving, by the implantable medical device, the indication of the therapy adjustment input from the external programmer.

9. The method of claim 1, further comprising generating a patient notification based on the physiological condition.

10. The method of claim 1, further comprising controlling, based on the physiological condition, a stimulation generator disposed within the implantable medical device to deliver electrical stimulation therapy via the implantable medical lead.

11. The method of claim 1, wherein producing the pressure wave comprises oscillating, with the actuator element, a free wall of the portion of the device housing of the implantable medical device.

12. A system comprising:
an implantable medical device comprising a device housing and configured to couple to an implantable medical lead;
an actuator element configured to contact a portion of the device housing to produce a pressure wave within a patient with the portion of the device housing, and wherein one of the actuator element or a detector element is configured to nd detect at least one reflected pressure wave with the portion of the device housing; and
a processor configured to determine a physiological condition of the patient based on the at least one reflected pressure wave, wherein the device housing encloses the processor and the actuator element.

13. The system of claim 12, wherein the implantable medical device comprises operational circuitry, the operational circuitry comprising the processor, wherein the device housing is configured to enclose the operational circuitry of the implantable medical device, and wherein the device housing is tuned to one or more frequencies of at least one of the produced pressure wave or the at least one reflected pressure wave.

14. The system of claim 12, wherein the implantable medical device is configured to be implanted at an internal location inferior to a bladder and lateral to a labia.

15. The system of claim 12, wherein the physiological condition includes a bladder fullness state.

16. The system of claim 12, further comprising an acoustic module comprising at least one of the actuator element or the detector element and one or more circuits, distinct from the processor the one or more circuits configured to:
determine a time delay between the produced pressure wave and the at least one reflected pressure wave; and
determine a distance between the portion of the device housing and an anatomical structure of the patient from which the at least one reflected pressure wave originated based on the time delay.

17. The system of claim 12, further comprising an acoustic module comprising at least one of the actuator element or the detector element and one or more circuits distinct from the processor, wherein the at least one reflected pressure wave comprises a first reflected pressure wave and a second reflected pressure wave, and wherein the one or more circuits are configured to:
determine a first time delay between the produced pressure wave and the first reflected pressure wave;
determine a second time delay between the produced pressure wave and the second reflected pressure wave; and
determine a distance between first and second anatomical structures of the patient from which the first and second reflected pressure waves, respectively, originated based on a difference between the first time delay and the second time delay.

18. The system of claim 12, further comprising an external programmer comprising a user interface, wherein the user interface is configured to receive a therapy adjustment input from the patient, the therapy adjustment input indicating an adjustment to therapy delivered by the implantable medical device.

19. The system of claim 18, further comprising a memory, wherein the processor is configured to:

determine the physiological condition with at least one of the actuator element or the detector element after an input delay period immediately following receipt of the therapy adjustment input by the external programmer and set the determined physiological condition as a first physiological state of the patient;

retrieve, from the memory, a last physiological condition determination before the therapy adjustment input was received; and set the last physiological condition determination as a second physiological state of the patient.

20. The system of claim 19, wherein the implantable medical device comprises the memory and a telemetry circuit configured to receive, from the external programmer, the adjustment to therapy indicated by the therapy adjustment input received by the external programmer.

21. The system of claim 12, further comprising an external programmer configured to present a notification to the patient based on the physiological condition.

22. The system of claim 12, further comprising:

the implantable medical lead coupled to the implantable medical device; and an electrical stimulation generator disposed within the device housing and configured to deliver electrical stimulation therapy to the patient via the implantable medical lead, wherein the processor is configured to control, based on the physiological condition, the electrical stimulation generator to deliver the electrical stimulation therapy.

23. The system of claim 12, wherein the portion of the device housing comprises a free wall configured to oscillate, and wherein the actuator element is configured to contact the free wall and produce the pressure wave with the free wall of the device housing by at least causing the free wall of the device housing to oscillate.

24. The system of claim 23, wherein the free wall is configured to move to produce the pressure wave and to detect the reflected pressure wave.

25. The system of claim 12, wherein the device housing, including the portion of the device housing, is constructed of a single metal alloy.

26. A system comprising:

means for producing a pressure wave within a patient with a portion of a device housing of an implantable medical device, wherein the housing encloses a processor and at least a portion of the means for producing the pressure wave with the portion of the device housing, and wherein the implantable medical device is configured to couple to an implantable medical lead, and detecting at least one reflected pressure wave with the portion of the housing; and means for determining, based on the at least one reflected pressure wave, a physiological condition of the patient.

27. The system of claim 26, wherein the device housing is configured to enclose operational circuitry of the implantable medical device, and wherein the portion of the device housing is tuned to one or more frequencies of at least one of the produced pressure wave or the at least one reflected pressure wave.

28. The system of claim 26, wherein the means for producing a pressure wave is configured to be implanted at an internal location inferior to a bladder and lateral to a labia.

29. The system of claim 26, further comprising:

means for delivering electrical stimulation therapy to the patient from the implantable medical device; and means for controlling, based on the physiological condition, the electrical stimulation therapy.

* * * * *